(12) United States Patent
Hwang et al.

(10) Patent No.: US 11,795,161 B2
(45) Date of Patent: Oct. 24, 2023

(54) COMPOUND AND ORGANIC LIGHT EMITTING DEVICE COMPRISING SAME

(71) Applicant: LG CHEM, LTD., Seoul (KR)

(72) Inventors: Sunghyun Hwang, Daejeon (KR); Dong Hoon Lee, Daejeon (KR); Boon Jae Jang, Daejeon (KR); Min Woo Jung, Daejeon (KR); Jungha Lee, Daejeon (KR); Su Jin Han, Daejeon (KR); Seulchan Park, Daejeon (KR)

(73) Assignee: LG CHEM, LTD., Seoul (KR)

( * ) Notice: Subject to any disclaimer, the term of this patent is extended or adjusted under 35 U.S.C. 154(b) by 520 days.

(21) Appl. No.: 17/044,789

(22) PCT Filed: Nov. 15, 2019

(86) PCT No.: PCT/KR2019/015682
§ 371 (c)(1),
(2) Date: Oct. 1, 2020

(87) PCT Pub. No.: WO2020/101439
PCT Pub. Date: May 22, 2020

(65) Prior Publication Data
US 2021/0107898 A1  Apr. 15, 2021

(30) Foreign Application Priority Data

Nov. 16, 2018 (KR) .......... 10-2018-0141846
Nov. 14, 2019 (KR) .......... 10-2019-0146190

(51) Int. Cl.
C07D 405/04 (2006.01)
C07D 405/10 (2006.01)
(Continued)

(52) U.S. Cl.
CPC ......... C07D 405/04 (2013.01); C07D 405/14 (2013.01); C07D 409/04 (2013.01);
(Continued)

(58) Field of Classification Search
CPC .. C07D 405/04; C07D 405/10; C07D 405/14; C07D 407/04; C07D 10/14
See application file for complete search history.

(56) References Cited

U.S. PATENT DOCUMENTS

2004/0251816 A1  12/2004  Leo et al.
2012/0205636 A1  8/2012  Kim et al.
(Continued)

FOREIGN PATENT DOCUMENTS

EP       2966706 A2    1/2016
KR  10-2000-0051826    8/2000
(Continued)

OTHER PUBLICATIONS

Machine-generated English-language translation of KR 2018-0073239 A to Kim et al.*
(Continued)

*Primary Examiner* — Vu A Nguyen
(74) *Attorney, Agent, or Firm* — Bryan Cave Leighton Paisner LLP

(57) ABSTRACT

A compound of the following Chemical Formula 1, and an organic light emitting device including the same.

(Continued)

Chemical Formula 1

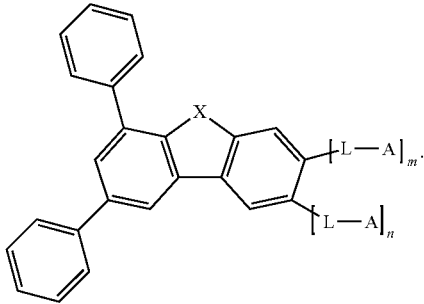

6 Claims, 2 Drawing Sheets

(51) Int. Cl.
    *C07D 405/14*     (2006.01)
    *C07D 409/04*     (2006.01)
    *C07D 409/10*     (2006.01)
    *C07D 409/14*     (2006.01)
    *C07D 495/04*     (2006.01)
    *H01L 51/00*     (2006.01)
    *H01L 51/50*     (2006.01)
    *H10K 85/60*     (2023.01)
    *H10K 50/15*     (2023.01)
    *H10K 50/16*     (2023.01)
    *H10K 50/18*     (2023.01)
    *H10K 50/17*     (2023.01)
(52) U.S. Cl.
    CPC ......... *C07D 409/14* (2013.01); *C07D 495/04* (2013.01); *H10K 85/654* (2023.02); *H10K 85/6572* (2023.02); *H10K 85/6574* (2023.02); *H10K 85/6576* (2023.02); *H10K 50/15* (2023.02); *H10K 50/16* (2023.02); *H10K 50/171* (2023.02); *H10K 50/18* (2023.02)

(56) References Cited

U.S. PATENT DOCUMENTS

| | | |
|---|---|---|
| 2013/0048964 A1 | 2/2013 | Takeda et al. |
| 2016/0028021 A1 | 1/2016 | Zeng et al. |
| 2016/0093808 A1 | 3/2016 | Adamovich et al. |
| 2016/0233436 A1 | 8/2016 | Zeng et al. |
| 2017/0054087 A1 | 2/2017 | Zeng et al. |
| 2017/0253796 A1 | 9/2017 | Takeda et al. |
| 2017/0294592 A1 | 10/2017 | Lee et al. |
| 2019/0047991 A1 | 2/2019 | Jung et al. |
| 2019/0259957 A1 | 8/2019 | Zeng et al. |
| 2019/0372012 A1 | 12/2019 | Cho et al. |

FOREIGN PATENT DOCUMENTS

| | | |
|---|---|---|
| KR | 10-2011-0043342 | 4/2011 |
| KR | 10-2013-0078437 | 7/2013 |
| KR | 10-2013-0094222 | 8/2013 |
| KR | 10-2016-0052200 | 5/2016 |
| KR | 10-2017-0057660 | 5/2017 |
| KR | 10-2018-0051355 | 5/2018 |
| KR | 10-1856728 | 5/2018 |
| KR | 10-2018-0073239 | 7/2018 |
| KR | 10-2020-0056589 A | 5/2020 |
| WO | 2003-012890 | 2/2003 |
| WO | 2011-162162 | 12/2011 |
| WO | 2013-027846 | 2/2013 |
| WO | 2013-100540 | 7/2013 |
| WO | 2018-084423 | 5/2018 |

OTHER PUBLICATIONS

Office Action of Korean Patent Office in Appl'n No. 10-2019-0146190, dated May 28, 2021.

\* cited by examiner

[FIG. 1]
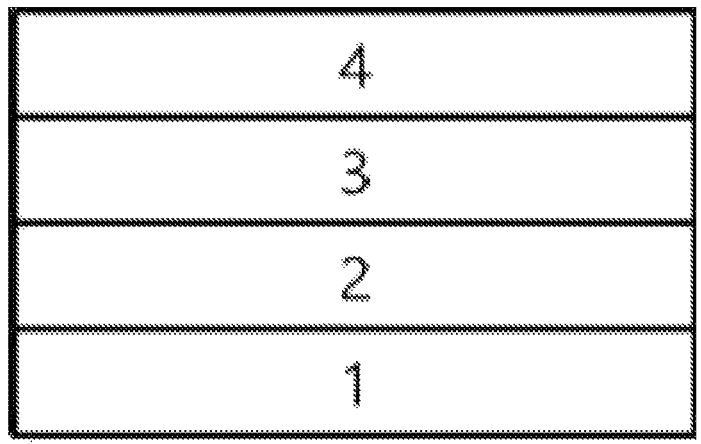
[FIG. 2]
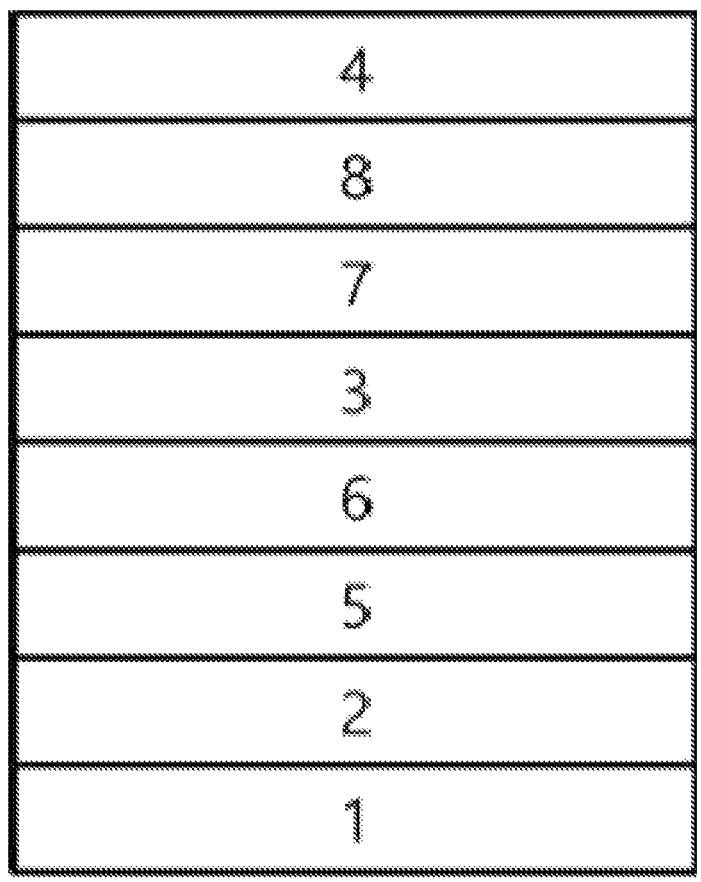

[FIG. 3]
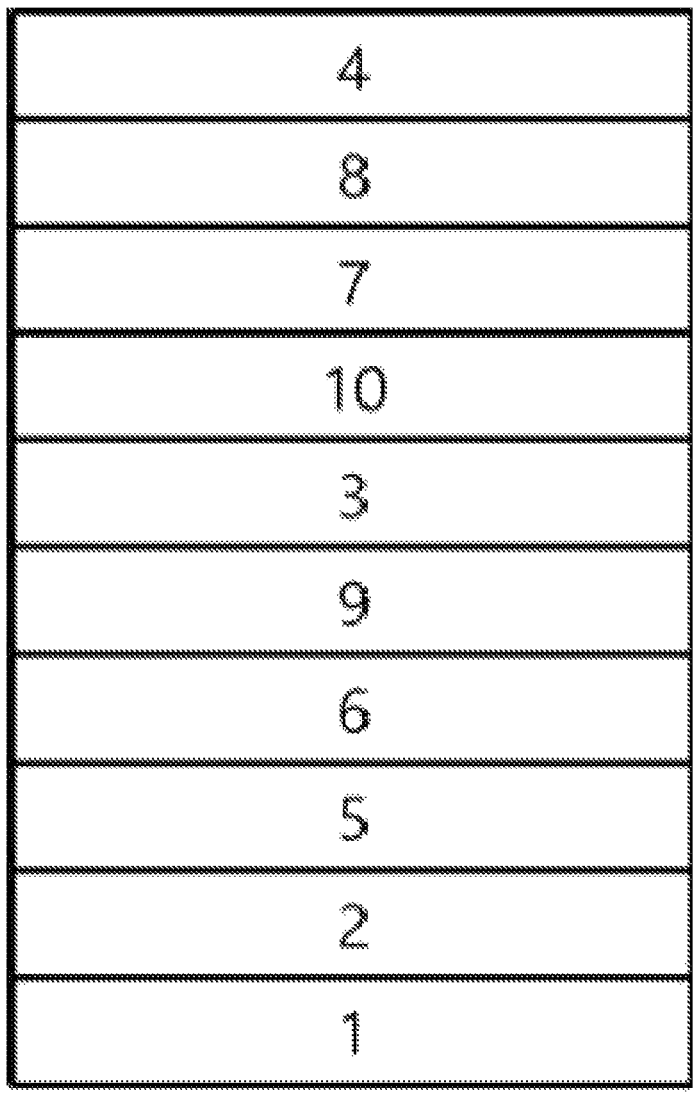

COMPOUND AND ORGANIC LIGHT EMITTING DEVICE COMPRISING SAME

CROSS-REFERENCE TO RELATED APPLICATION(S)

This application is a National Stage Application of International Application No. PCT/KR2019/015682, filed on Nov. 15, 2019, which claims priority to or the benefit of Korean Patent Application No. 10-2018-0141846 filed with the Korean Intellectual Property Office on Nov. 16, 2018, and Korean Patent Application No. 10-2019-0146190 filed with the Korean Intellectual Property Office on Nov. 14, 2019, the disclosures of which are incorporated herein by reference in their entirety.

TECHNICAL FIELD

The present disclosure relates to a novel compound and an organic light emitting device including the same.

BACKGROUND

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer may be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in the organic light emitting devices as described above.

(Patent Literature 1) Korean Unexamined Patent Publication No. 10-2000-0051826

Technical Problem

It is an object of the present disclosure to provide a novel organic light emitting material and an organic light emitting device including the same.

Technical Solution

One aspect of the present disclosure provides a compound of the following Chemical Formula 1:

Chemical Formula 1

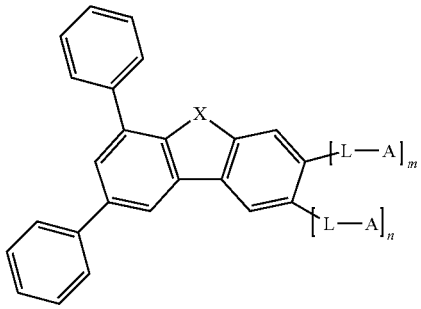

wherein, in Chemical Formula 1, m and n are each independently 0 or 1, with the proviso that at least one of m and n is 1, X is O or S, L is a single bond; a substituted or unsubstituted $C_{6-60}$ arylene; or a substituted or unsubstituted $C_{2-60}$ heteroarylene containing any one or more selected from the group consisting of N, O and S, A is any one selected from the group consisting of the following:

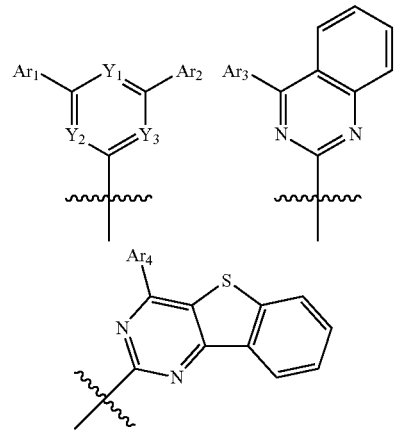

$Y_1$ to $Y_3$ are each independently N or CH, with the proviso that at least two of $Y_1$ to $Y_3$ are N, and $Ar_1$ to $Ar_4$ are each independently a substituted or unsubstituted $C_{6-60}$ aryl; or a substituted or unsubstituted $C_{2-60}$ heteroaryl containing any one or more selected from the group consisting of N, O and S.

Another aspect of the present disclosure provides an organic light emitting device including a first electrode; a second electrode that is disposed opposite to the first electrode; and one or more organic material layers that are disposed between the first electrode and the second electrode, wherein one or more layers of the organic material layers include the compound of Chemical Formula 1.

Advantageous Effects

The compound of Chemical Formula 1 described above can be used as a material of an organic material layer of an organic light emitting device and may improve the efficiency, achieve low driving voltage and/or improve lifetime characteristics in the organic light emitting device. In particular, the compound of Chemical Formula 1 may be used as a hole injection material, hole transport material, hole injection and transport material, light emitting material, electron transport material, or electron injection material.

BRIEF DESCRIPTION OF THE DRAWINGS

FIG. 1 shows an example of an organic light emitting device comprising a substrate 1, an anode 2, a light emitting layer 3, and a cathode 4.

FIG. 2 shows an example of an organic light emitting device comprising a substrate 1, an anode 2, a hole injection layer 5, a hole transport layer 6, a light emitting layer 3, an electron transport layer 7, an electron injection layer 8, and a cathode 4.

FIG. 3 shows an example of an organic light emitting device comprising a substrate 1, an anode 2, a hole injection layer 5, a hole transport layer 6, an electron blocking layer 9, a light emitting layer 3, a hole blocking layer 10, an electron transport layer 7, an electron injection layer 8, and a cathode 4.

DETAILED DESCRIPTION

Hereinafter, embodiments of the present disclosure will be described in more detail to facilitate understanding of the invention.

One embodiment of the invention provides a compound of Chemical Formula 1.

As used herein, the notation

means a bond linked to another substituent group.

As used herein, the term "substituted or unsubstituted" means being unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; or a heterocyclic group containing at least one of N, O and S atoms, or being unsubstituted or substituted with a substituent to which two or more substituents are linked among the substituents exemplified above. For example, "the substituent to which two or more substituents are linked" may be a biphenyl group. That is, the biphenyl group may also be an aryl group and may be interpreted as a substituent to which two phenyl groups are linked.

In the present specification, the number of carbon atoms of a carbonyl group is not particularly limited, but is preferably 1 to 40. Specifically, the carbonyl group may be a compound having the following structural formulae but is not limited thereto.

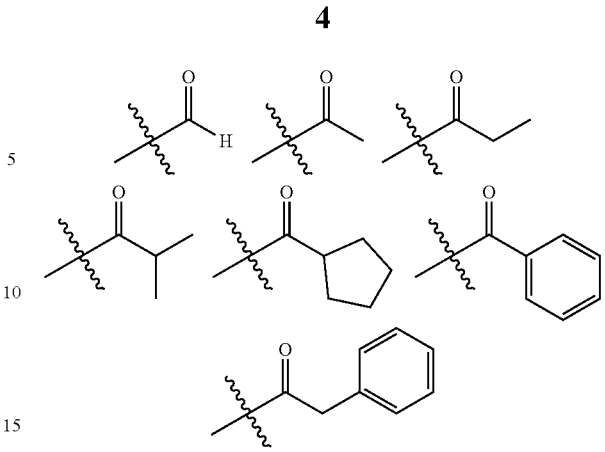

In the present specification, an ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be a compound having the following structural formulae, but is not limited thereto.

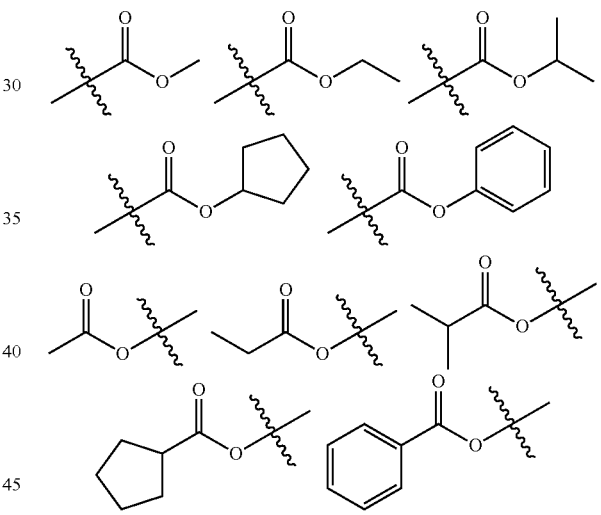

In the present specification, the number of carbon atoms of an imide group is not particularly limited, but is preferably 1 to 25. Specifically, the imide group may be a compound having the following structural formulae, but is not limited thereto.

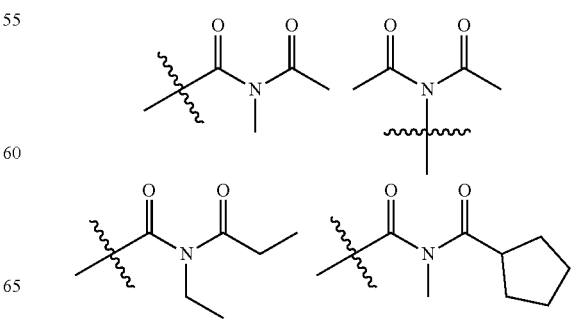

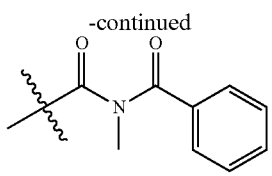

In the present specification, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present specification, a boron group specifically includes a trimethylboron group, a triethylboron group, a t-butyldimethylboron group, a triphenylboron group, and a phenylboron group, but is not limited thereto.

In the present specification, examples of a halogen group include fluorine, chlorine, bromine, or iodine.

In the present specification, the alkyl group may be a straight-chain or branched chain, and the number of carbon atoms thereof is not particularly limited, but is preferably 1 to 40. According to one embodiment, the number of carbon atoms of the alkyl group is 1 to 20. According to another embodiment, the number of carbon atoms of the alkyl group is 1 to 10. According to another embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the alkenyl group may be a straight chain or branched chain, and the number of carbon atoms thereof is not particularly limited, but is preferably 2 to 40. According to one embodiment, the number of carbon atoms of the alkenyl group is 2 to 20. According to another embodiment, the number of carbon atoms of the alkenyl group is 2 to 10. According to still another embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the number of carbon atoms of the cycloalkyl group is 3 to 30. According to another embodiment, the number of carbon atoms of the cycloalkyl group is 3 to 20. According to still another embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an aryl group is not particularly limited, but preferably has 6 to 60 carbon atoms, and may be a monocyclic aryl group or a polycyclic aryl group. According to one embodiment, the number of carbon atoms of the aryl group is 6 to 30. According to one embodiment, the number of carbon atoms of the aryl group is 6 to 20. The aryl group may be a phenyl group, a biphenyl group, a terphenyl group or the like as the monocyclic aryl group, but is not limited thereto. Examples of the polycyclic aryl group include a naphthyl group, an anthracenyl group, a phenanthryl group, a pyrenyl group, a perylenyl group, a chrysenyl group, a fluorenyl group or the like, but is not limited thereto.

In the present specification, a fluorenyl group may be substituted, and two substituent groups may be connected with each other to form a spiro structure. In the case where the fluorenyl group is substituted,

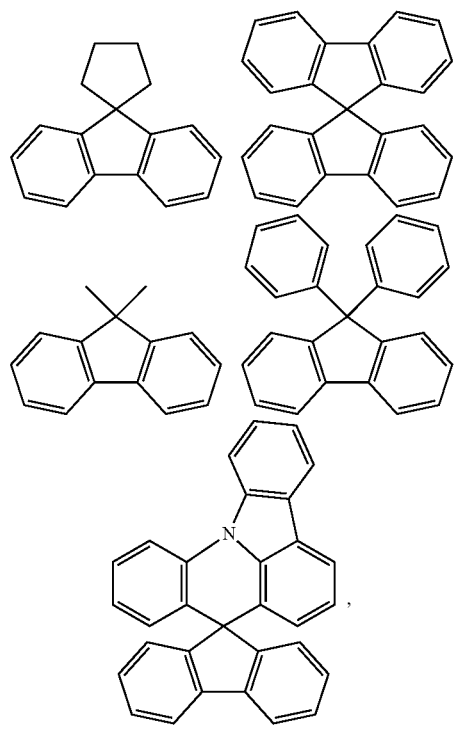

and the like can be formed. However, the structure is not limited thereto.

In the present specification, a heterocyclic group is a heterocyclic group including one or more of O, N, Si, and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazol group, a benzocarbazole group, a benzothiophene group, a dibenzothiophene group, a benzofuranyl group, a phenanthroline group, an isoxazolyl group, an thiadiazolyl group, a phenothiazinyl group, a dibenzofuranyl group, and the like, but are not limited thereto.

In the present specification, the aryl group in the aralkyl group, the aralkenyl group, the alkylaryl group, and the arylamine group is the same as the aforementioned examples of the aryl group. In the present specification, the alkyl group in the aralkyl group, the alkylaryl group and the alkylamine group is the same as the aforementioned examples of the alkyl group. In the present specification, the heteroaryl in the heteroarylamine can be applied to the aforementioned description of the heteroaryl. In the present specification, the alkenyl group in the aralkenyl group is the same as the aforementioned examples of the alkenyl group. In the present specification, the aforementioned description of the aryl group may be applied except that the arylene is a divalent group. In the present specification, the aforementioned description of the heteroaryl can be applied except that the heteroarylene is a divalent group. In the present specification, the aforementioned description of the aryl group or cycloalkyl group can be applied except that the hydrocarbon ring is not a monovalent group but formed by combining two substituent groups. In the present specification, the aforementioned description of the heteroaryl can be applied, except that the heterocycle is not a monovalent group but formed by combining two substituent groups.

The above-mentioned compound may be one of the following Chemical Formula 1-1 or 1-2:

Chemical Formula 1-1

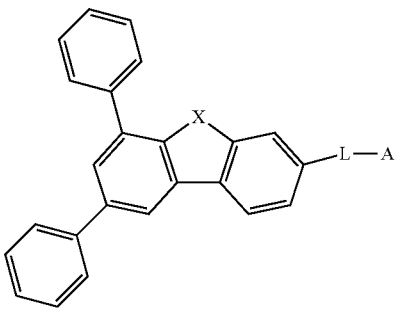

Chemical Formula 1-2

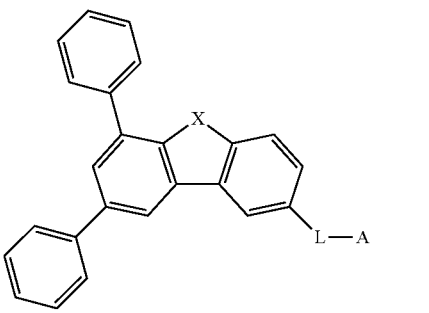

wherein, in Chemical Formula 1-1 or 1-2,

X, L and A are the same as defined in Chemical Formula 1.

Preferably, L is a single bond; a substituted or unsubstituted $C_{6-20}$ arylene; or a substituted or unsubstituted $C_{6-20}$ heteroarylene containing any one or more selected from the group consisting of N, O and S.

More preferably, L may be a single bond or phenylene.

Preferably, $Ar_1$ to $Ar_4$ may be each independently a substituted or unsubstituted $C_{6-20}$ aryl; or a substituted or unsubstituted $C_{6-20}$ heteroaryl containing any one or more selected from the group consisting of N, O and S.

More preferably, $Ar_1$ to $Ar_4$ may be each independently phenyl, biphenylyl, dibenzofuranyl, dibenzothiophenyl, phenyl carbazolyl, or carbazolyl phenyl.

Preferably, at least one of $Ar_1$ and $Ar_2$ may be a substituted or unsubstituted $C_{6-60}$ aryl.

More preferably, at least one of $Ar_1$ and $Ar_2$ may be a substituted or unsubstituted $C_{6-20}$ aryl.

Most preferably, at least one of $Ar_1$ and $Ar_2$ may be phenyl.

Representative examples of the compound of Chemical Formula 1 are as follows:

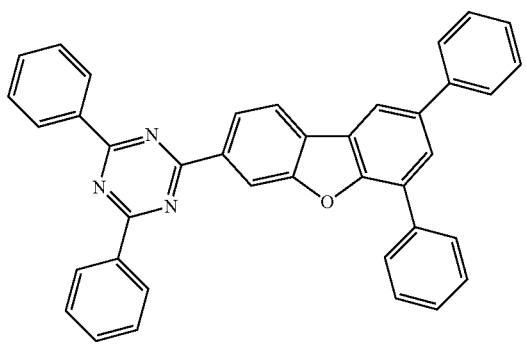

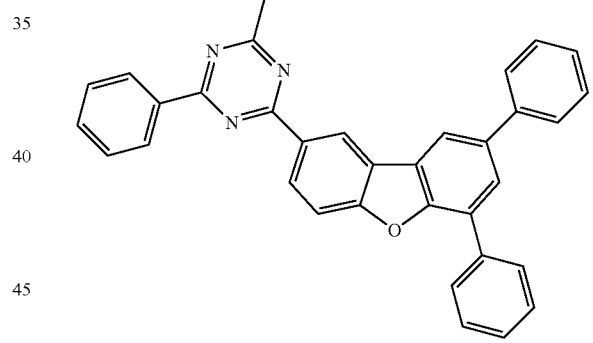

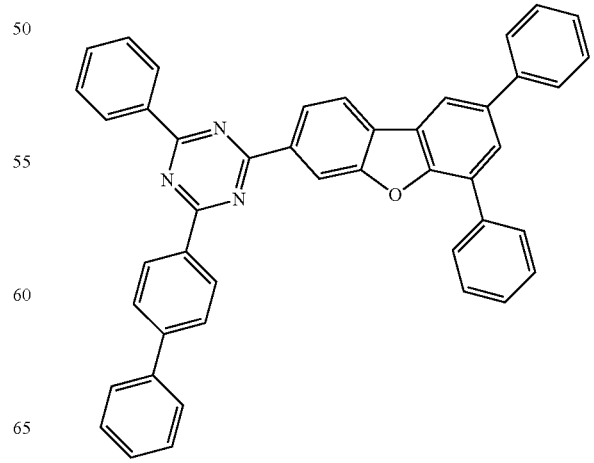

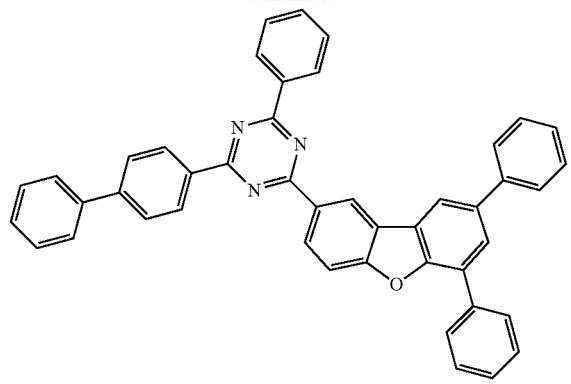
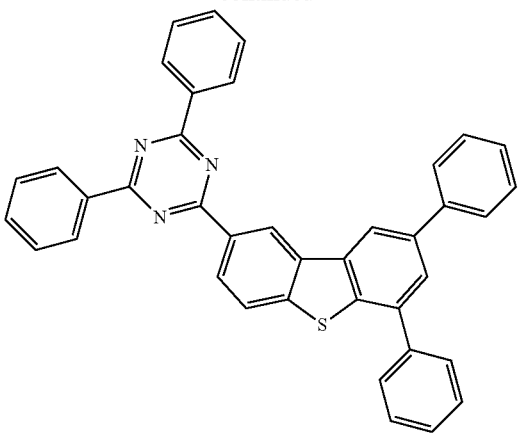
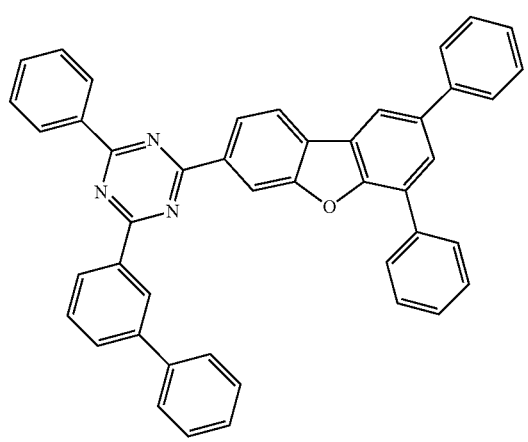
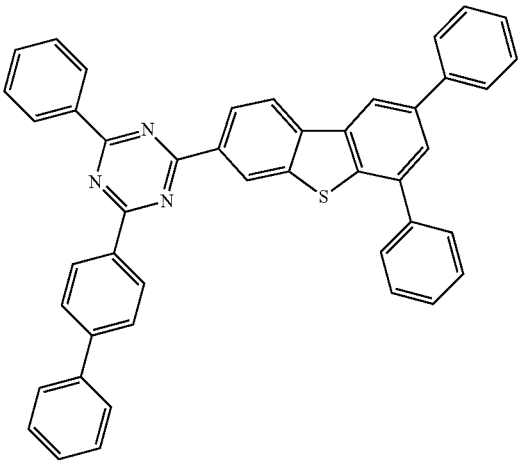
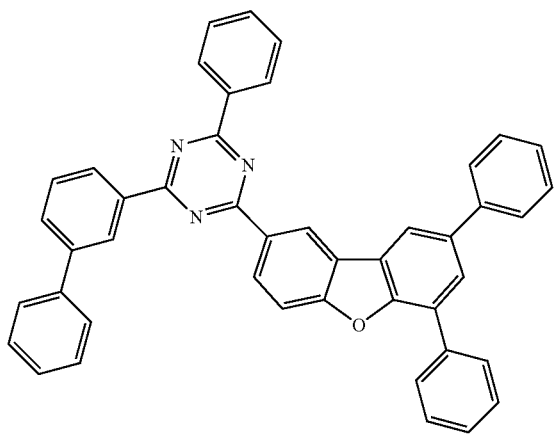
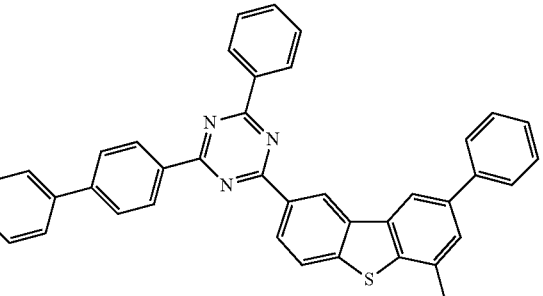
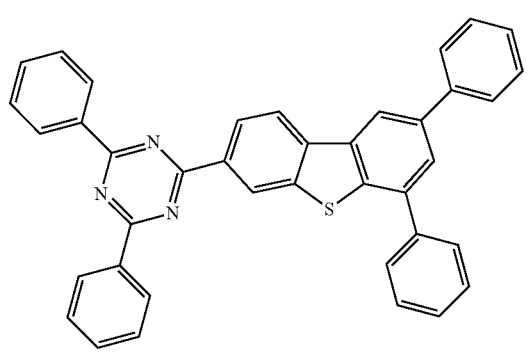
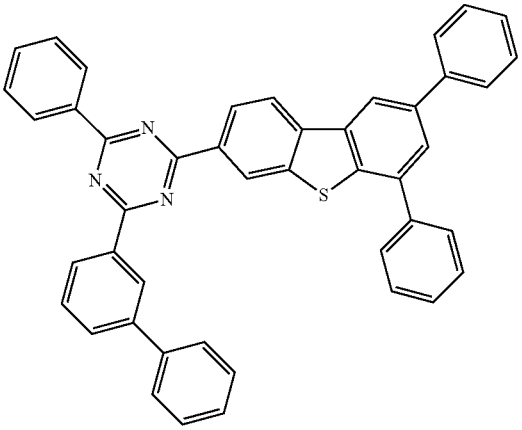

-continued
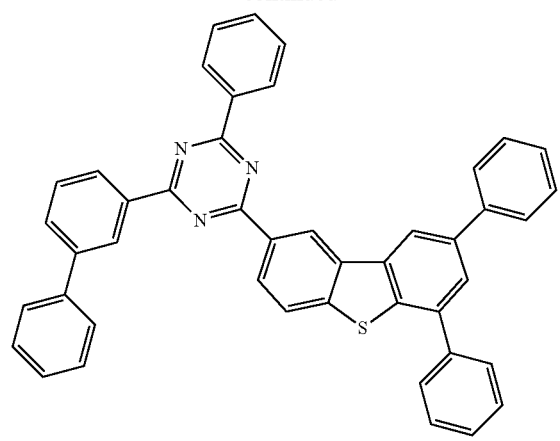
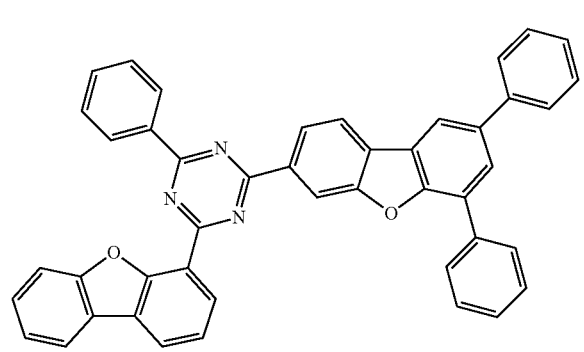
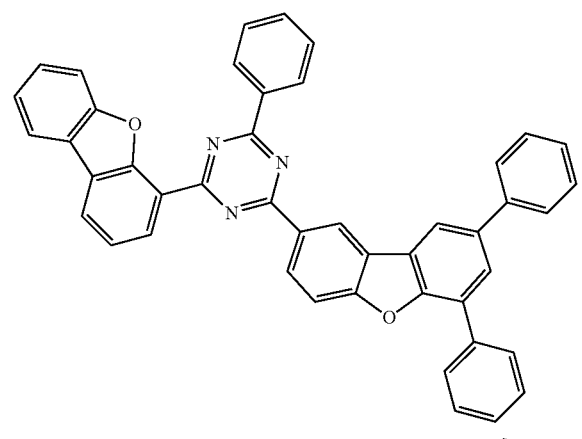
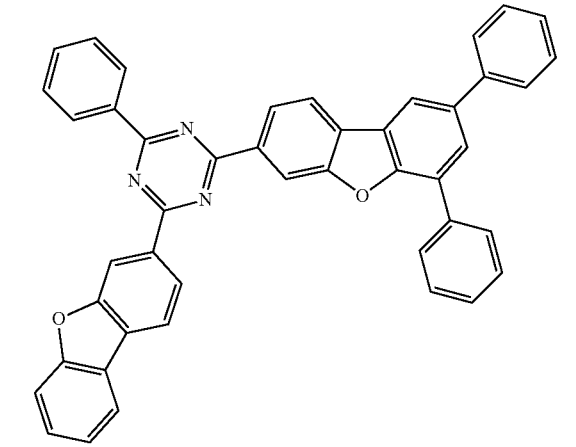
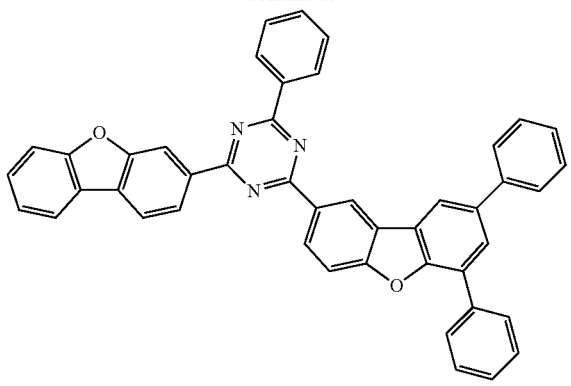
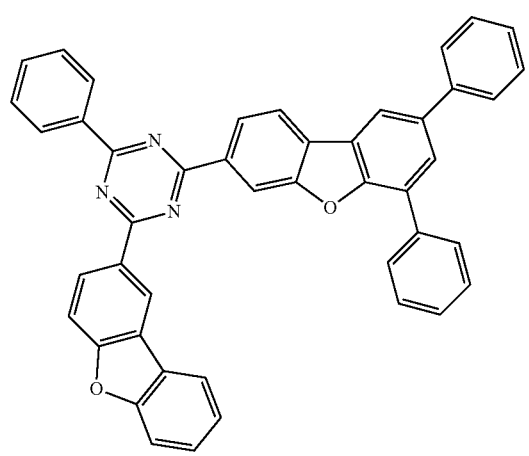
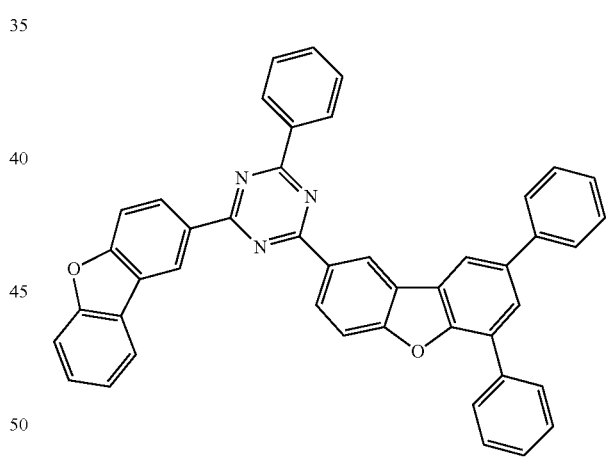
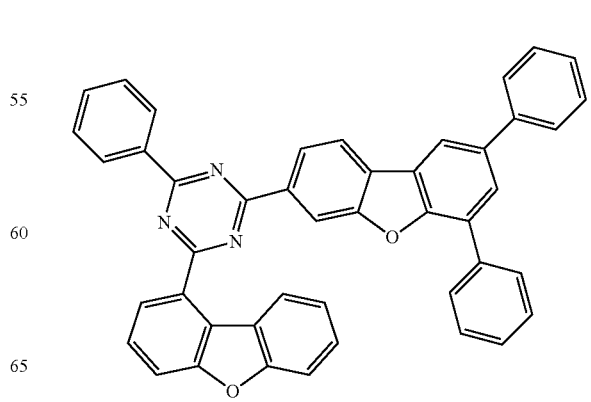

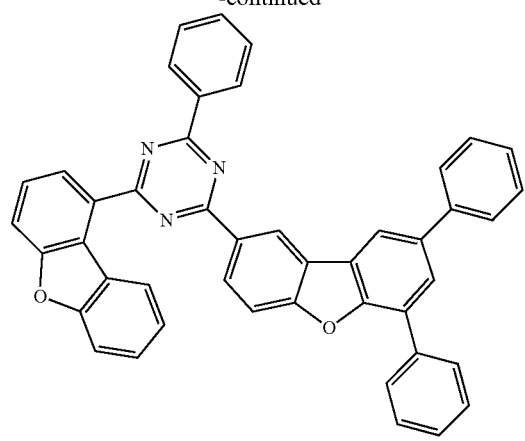
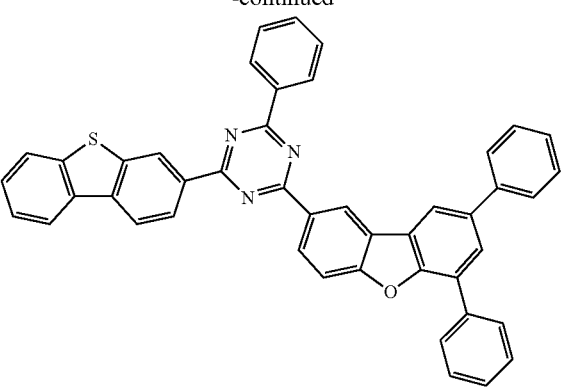
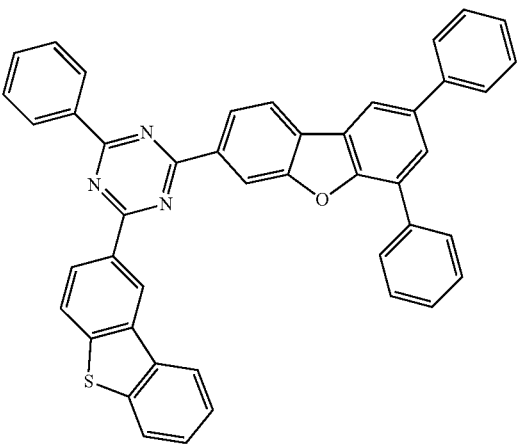
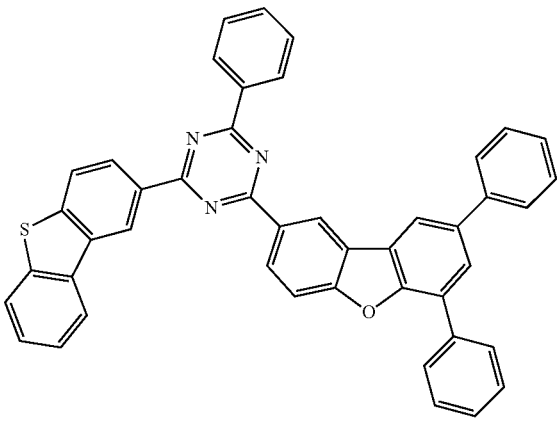
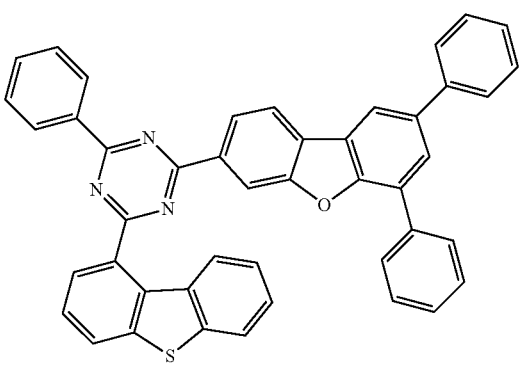

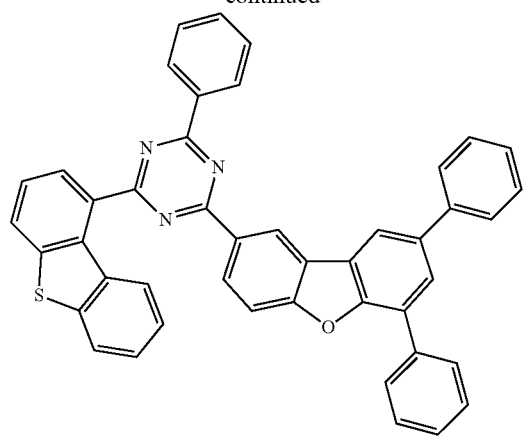
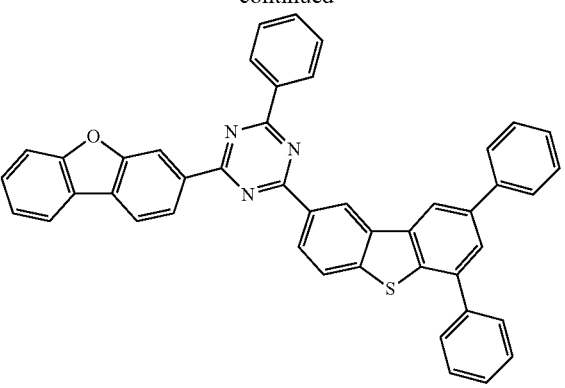

17
-continued
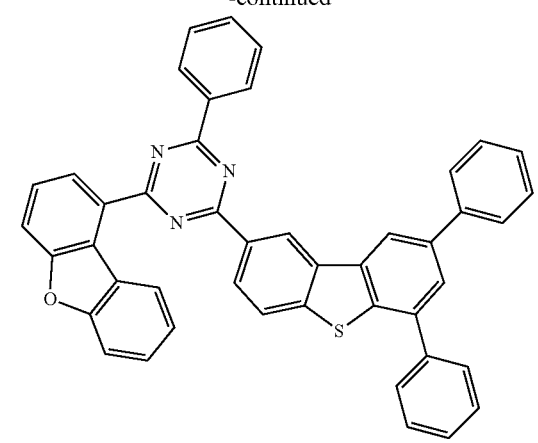
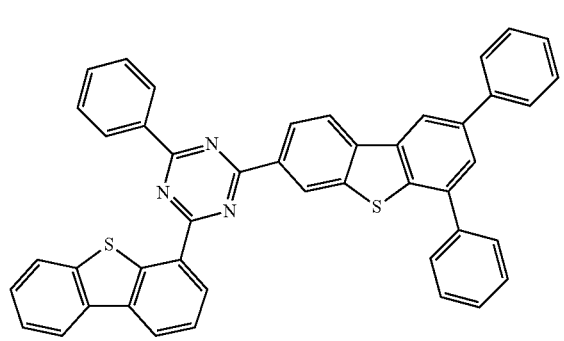
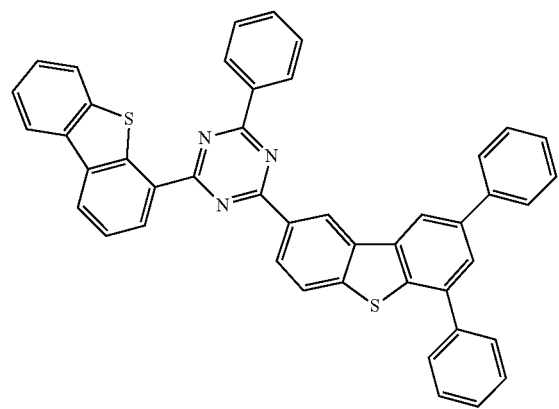
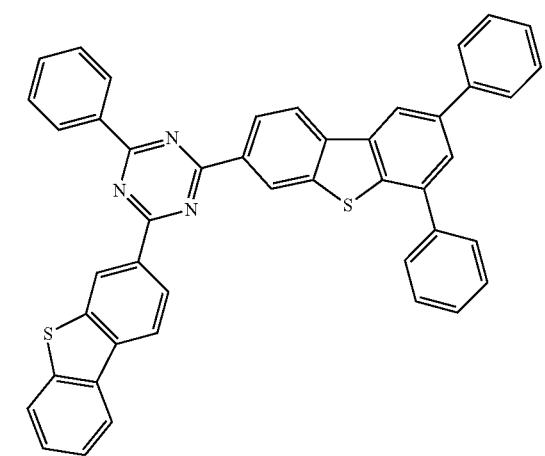
18
-continued
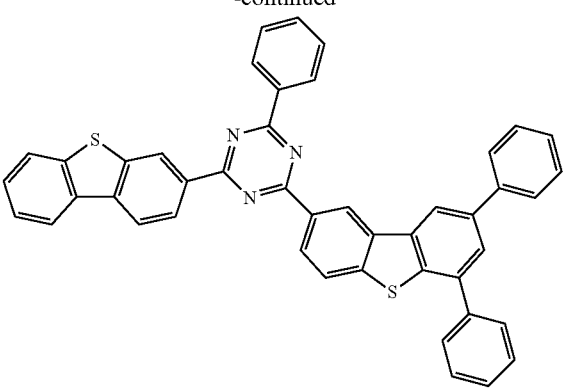
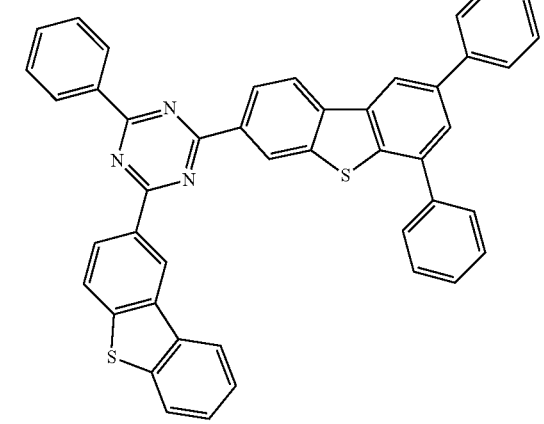
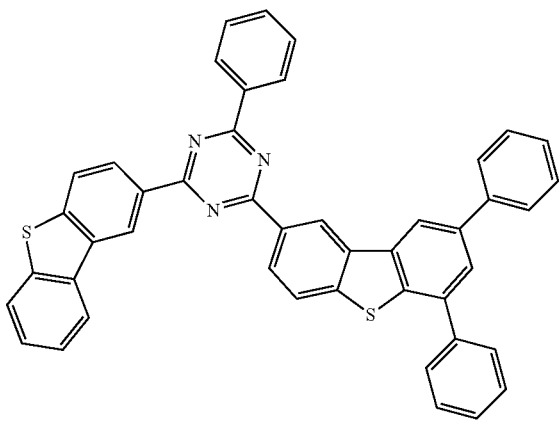
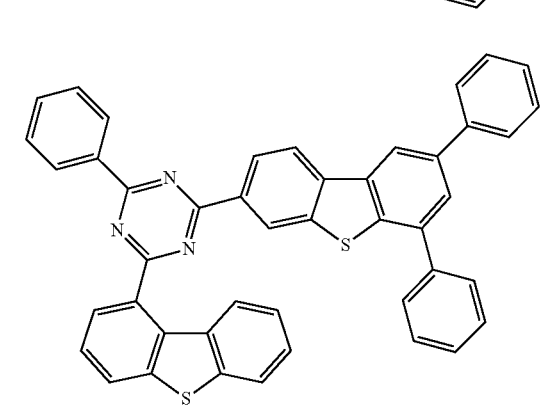

-continued
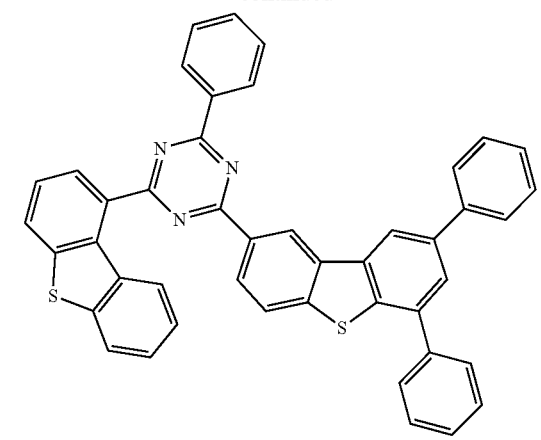
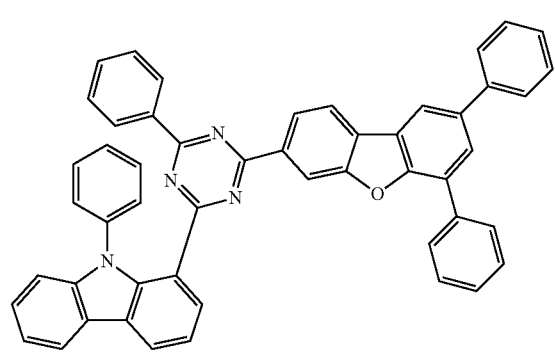
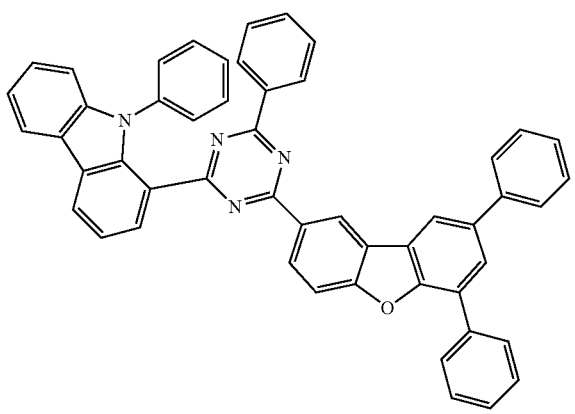
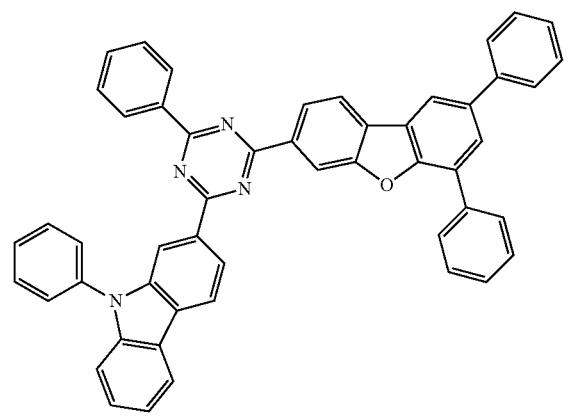
-continued
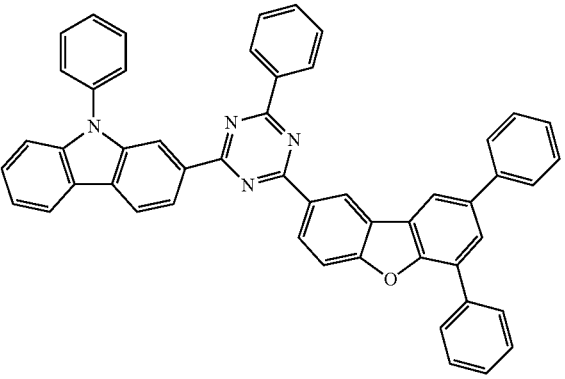
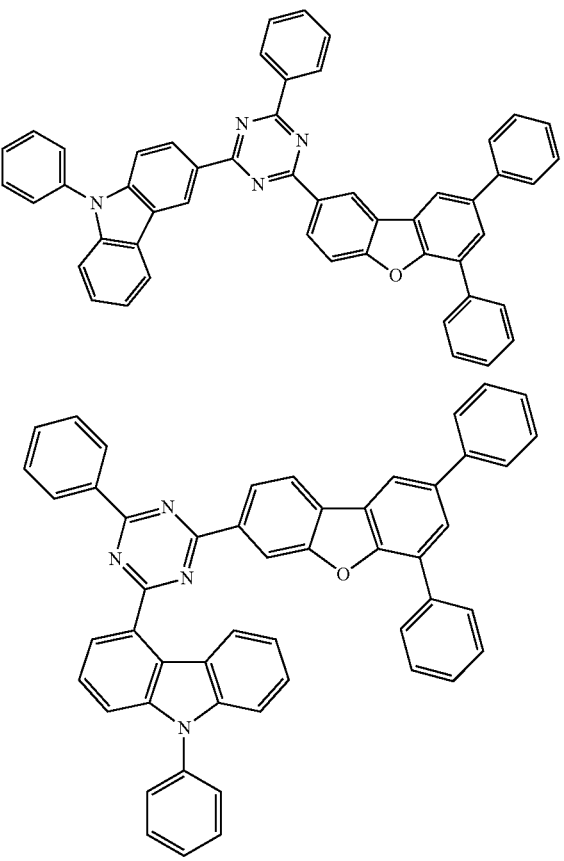

-continued
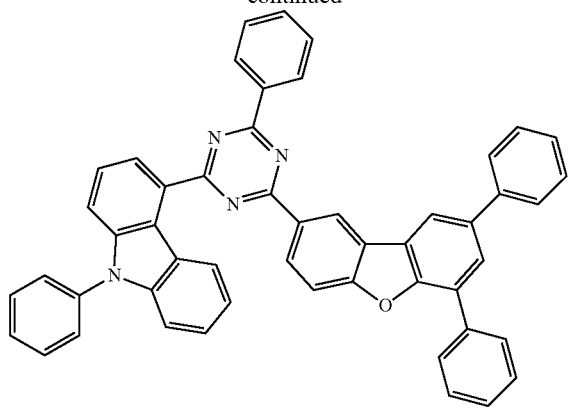
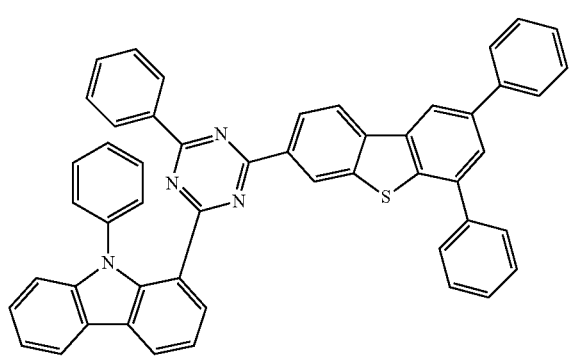
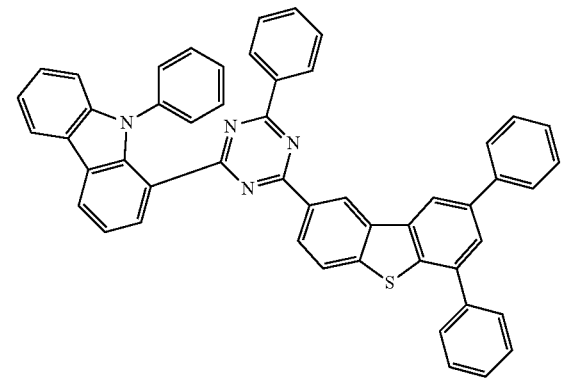
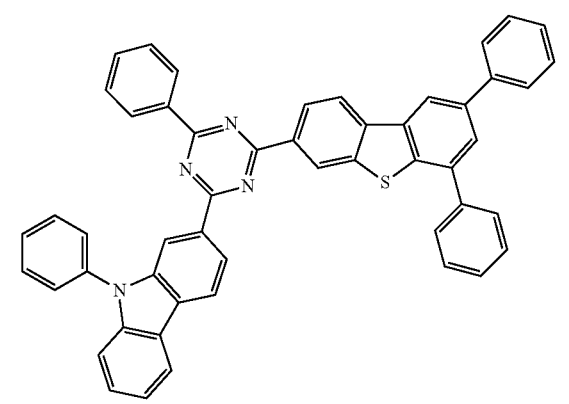
-continued
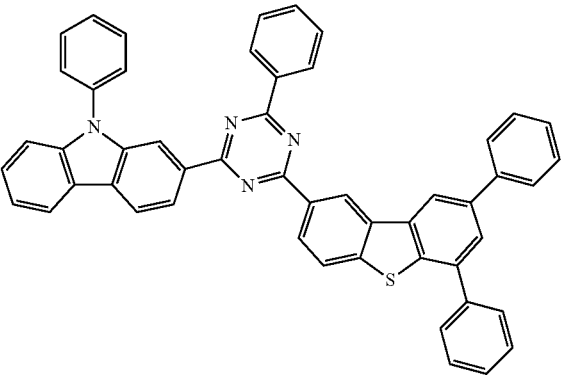
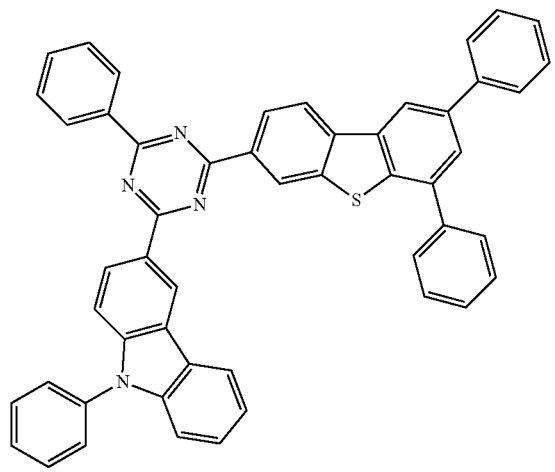
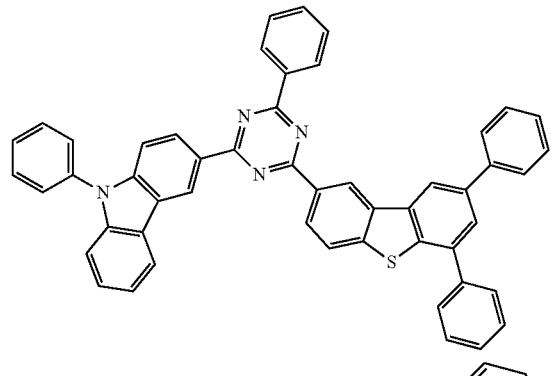

-continued
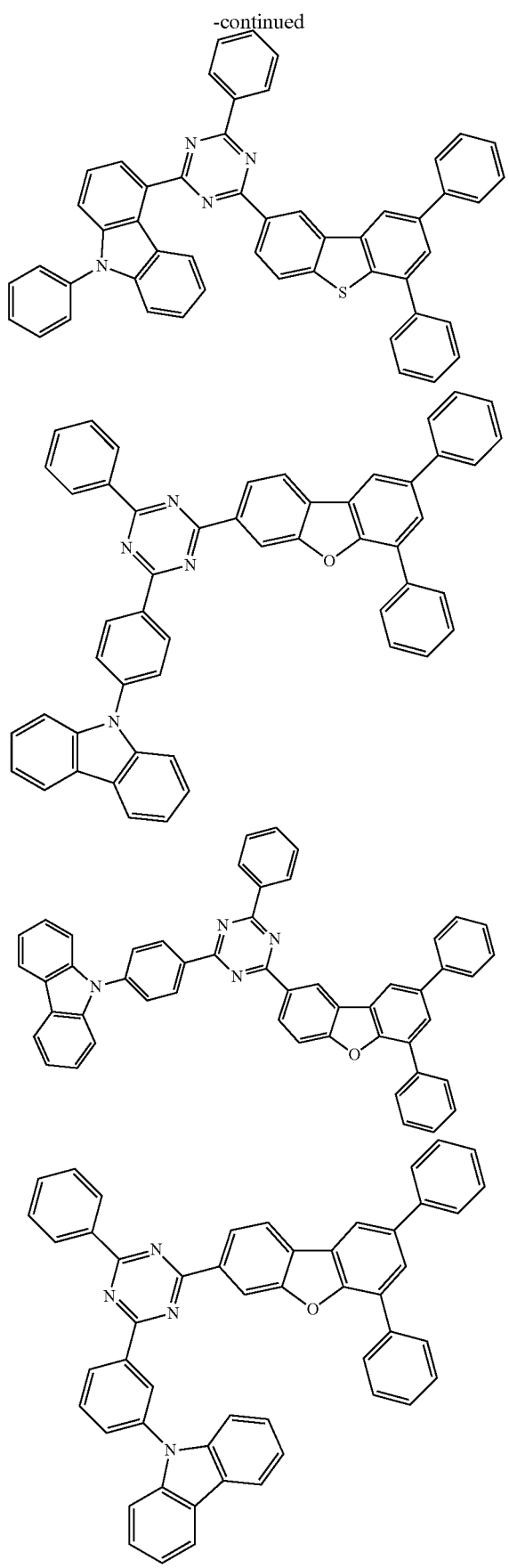
-continued
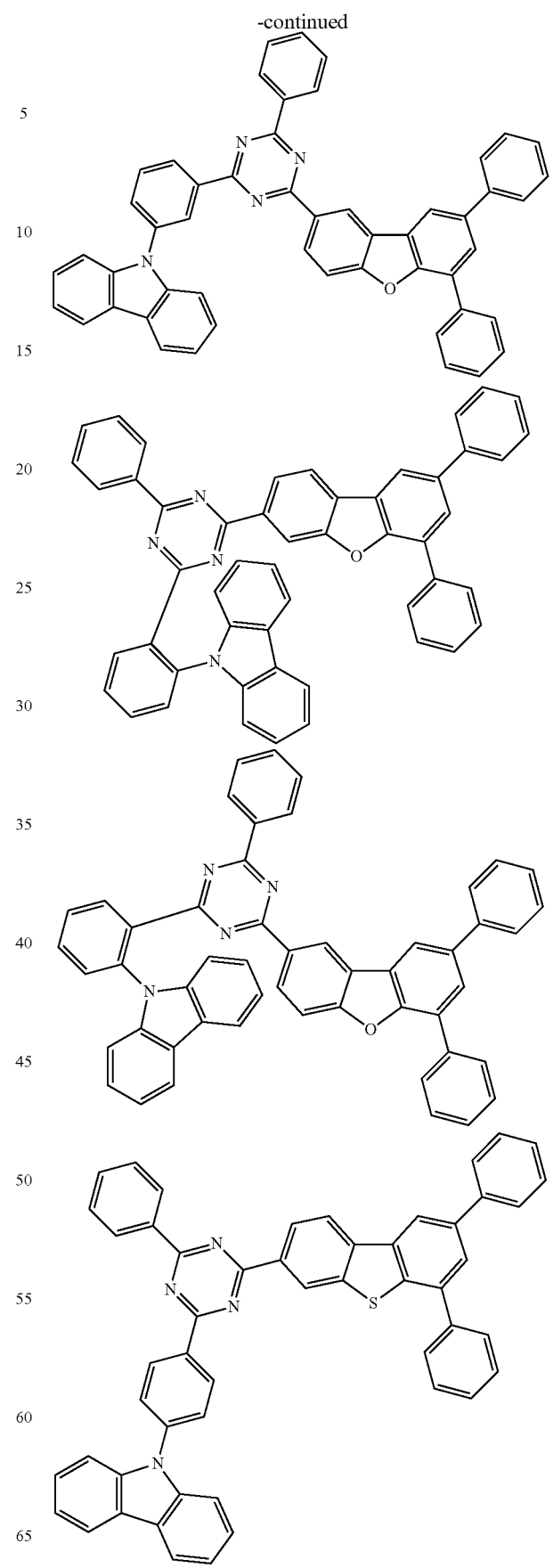

-continued
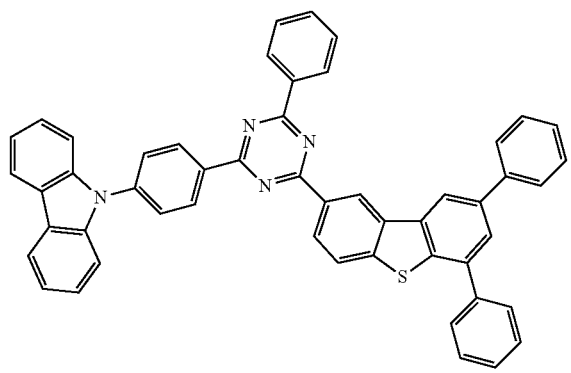
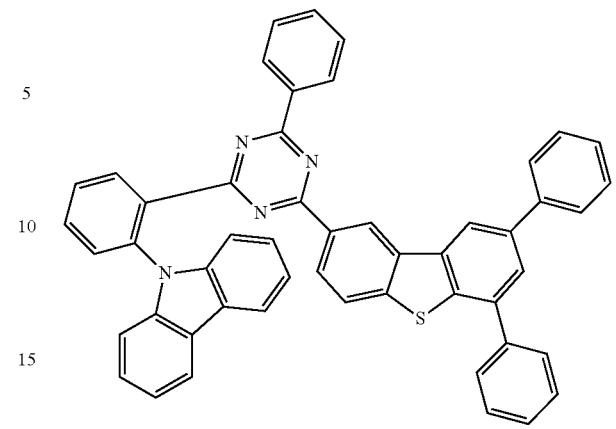
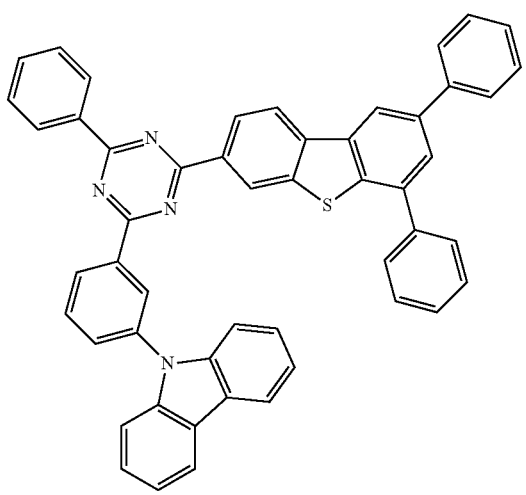
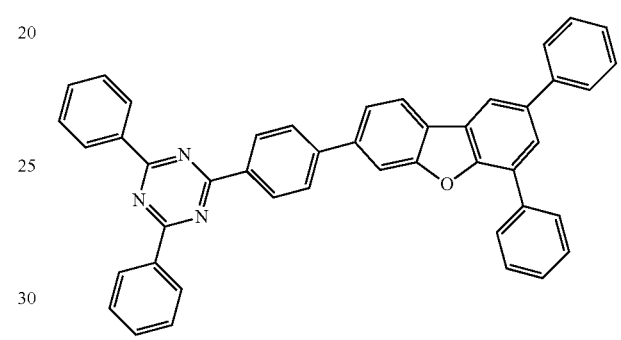
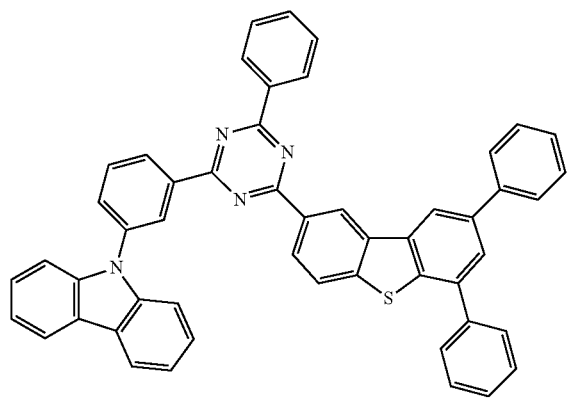
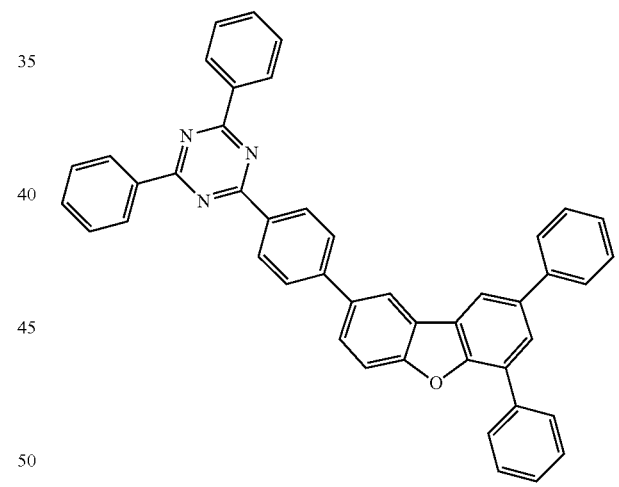
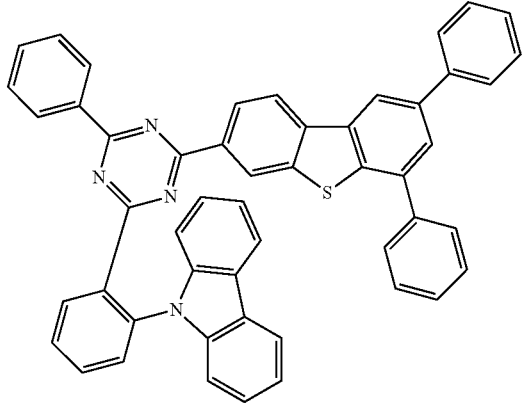
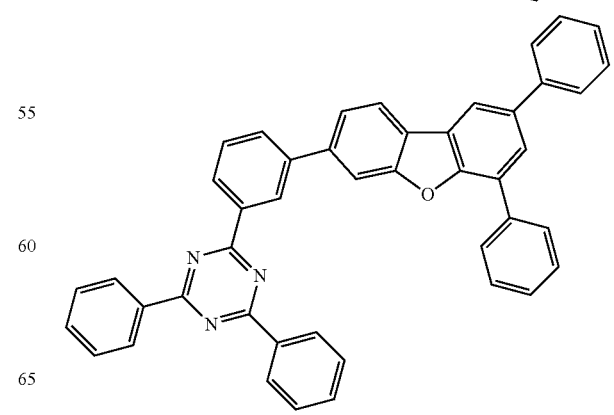

27
-continued
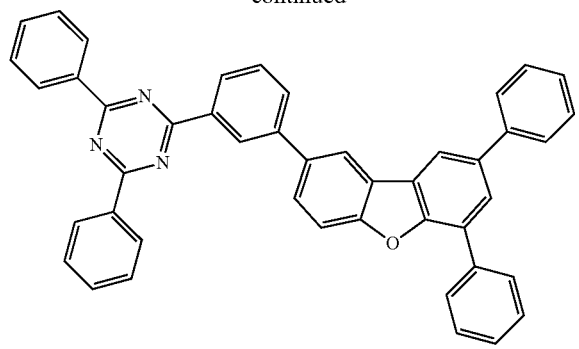
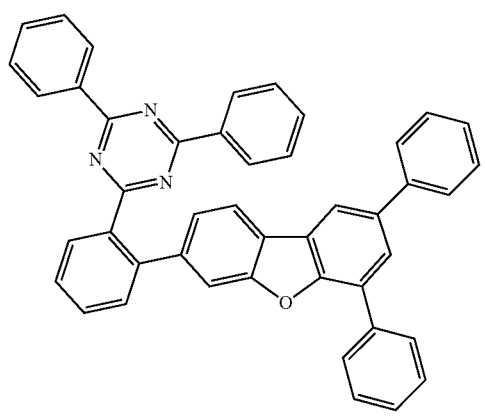
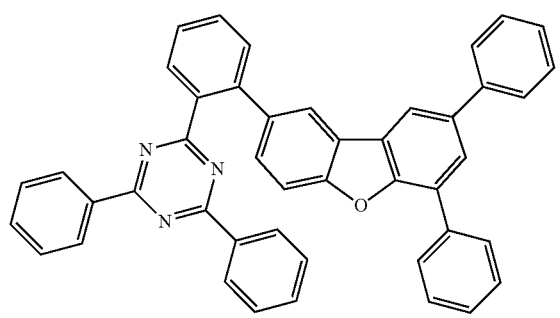
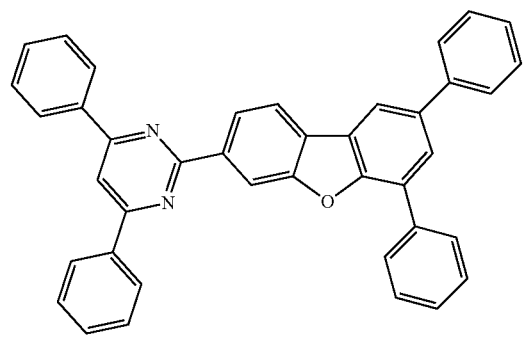
28
-continued
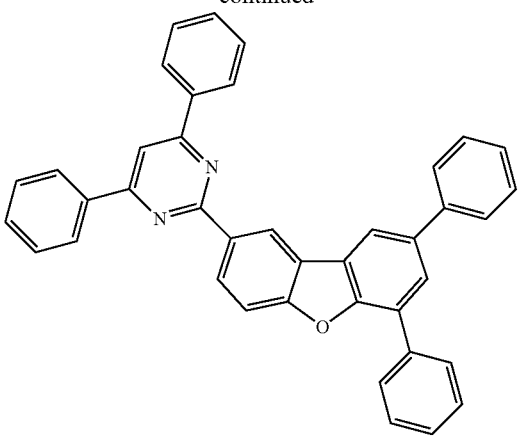
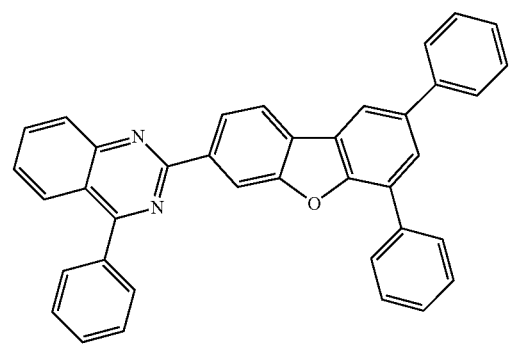
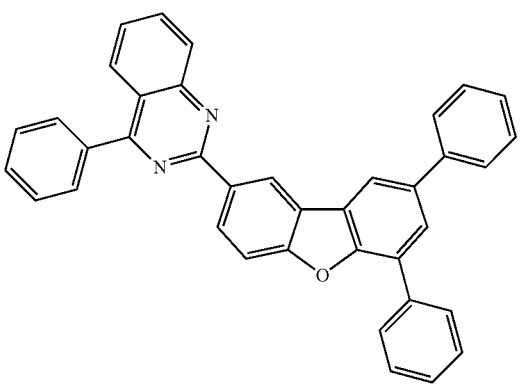
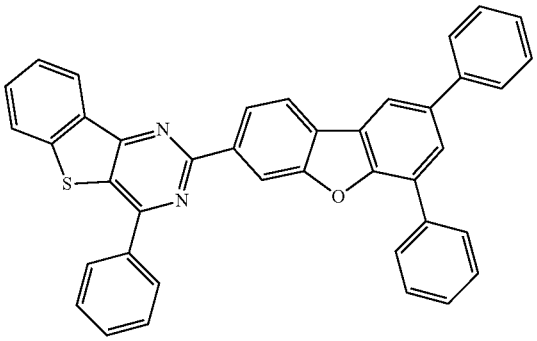

-continued

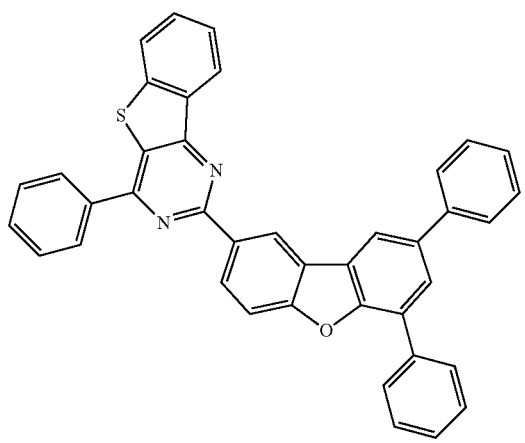

The compound of Chemical Formula 1 where n is 0 may be prepared, for example, in accordance with a preparation method as shown in Reaction Scheme 1 below, the compound of Chemical Formula 1 where m is 0 may be prepared in accordance with a preparation method as shown in Reaction Scheme 2 below, and the other remaining compounds can be prepared in a similar manner.

Reaction Scheme 1

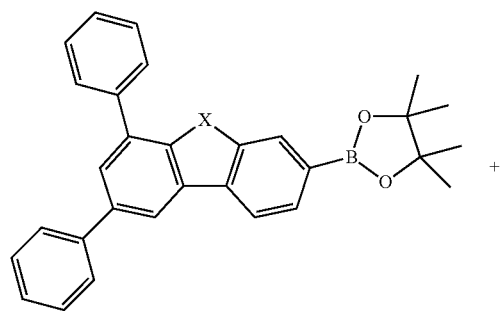

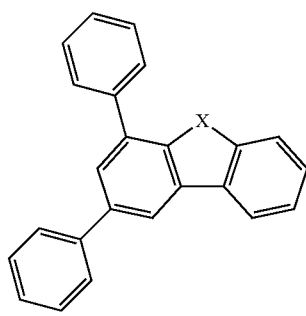

Reaction Scheme 2

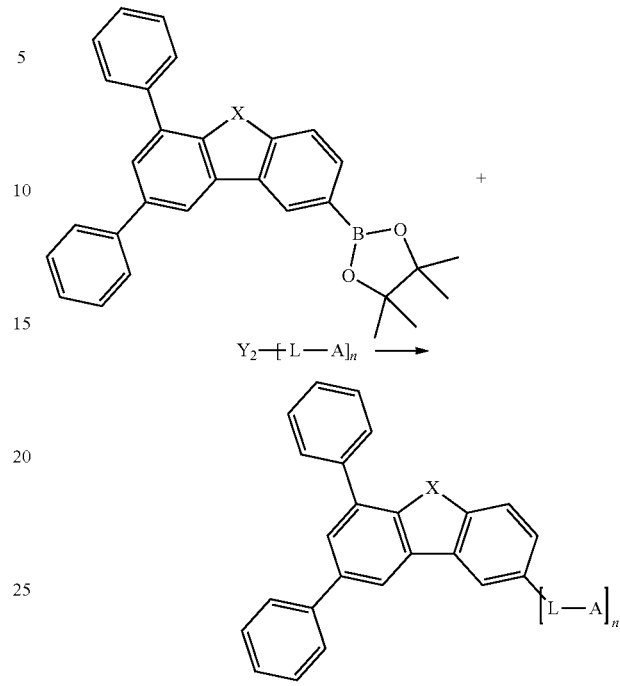

In Reaction Schemes 1 and 2, X, L, A, m and n are the same as defined in Chemical Formula 1, $Y_1$ and $Y_2$ are halogen, and more preferably $Y_1$ and $Y_2$ are bromo or chloro.

Reaction Scheme 1 and Reaction Scheme 2 are Suzuki coupling reactions, which are preferably carried out in the presence of a palladium catalyst and a base, and a reactive group for the Suzuki coupling reaction can be modified as known in the art. The above preparation method may be further embodied in the Preparation Examples described hereinafter.

Another embodiment of the invention provides an organic light emitting device including a compound of Chemical Formula 1 described above. As an example, there is provided an organic light emitting device including a first electrode; a second electrode that is disposed opposite to the first electrode; and one or more organic material layers that are disposed between the first electrode and the second electrode, wherein one or more layers of the organic material layers include the compound of Chemical Formula 1.

The organic material layer of the organic light emitting device of the present disclosure may have a single-layer structure, or it may have a multilayered structure in which two or more organic material layers are stacked. For example, the organic light emitting device of the present disclosure may have a structure comprising a hole injection layer, a hole transport layer, a light emitting layer, an electron transport layer, an electron injection layer and the like as the organic material layer. However, the structure of the organic light emitting device is not limited thereto, and it may include a smaller number of organic layers.

Further, the organic material layer may include a light emitting layer, wherein the light emitting layer includes the compound of Chemical Formula 1. In particular, the compound according to the present disclosure can be used as a host of the light emitting layer.

Further, the organic material layer may include an electron transport layer, or an electron injection layer, wherein the electron transport layer, or the electron injection layer may include the compound of Chemical Formula 1.

In addition, the electron transport layer, the electron injection layer, or a layer for simultaneously performing electron transport and electron injection include a compound of Chemical Formula 1.

Further, the organic material layer includes a light emitting layer and an electron transport layer, wherein the electron transport layer may include a compound of Chemical Formula 1.

Further, the organic light emitting device according to the present disclosure may be a normal type organic light emitting device in which an anode, one or more organic material layers, and a cathode are sequentially stacked on a substrate. Further, the organic light emitting device according to the present disclosure may be an inverted type organic light emitting device in which a cathode, one or more organic material layers, and an anode are sequentially stacked on a substrate. For example, the structure of an organic light emitting device according to an embodiment of the present disclosure is illustrated in FIGS. 1 and 2.

FIG. 1 shows an example of an organic light emitting device comprising a substrate 1, an anode 2, a light emitting layer 3, and a cathode 4. In such a structure, the compound of Chemical Formula 1 may be included in the light emitting layer.

FIG. 2 shows an example of an organic light emitting device comprising a substrate 1, an anode 2, a hole injection layer 5, a hole transport layer 6, a light emitting layer 3, an electron transport layer 7, an electron injection layer 8, and a cathode 4. In such a structure, the compound of Chemical Formula 1 may be included in one or more layers of the hole injection layer, the hole transport layer, the light emitting layer and the electron transport layer.

FIG. 3 shows an example of an organic light emitting device comprising a substrate 1, an anode 2, a hole injection layer 5, a hole transport layer 6, an electron blocking layer 9, a light emitting layer 3, a hole blocking layer 10, an electron transport layer 7, an electron injection layer 8, and a cathode 4. In such a structure, the compound of Chemical Formula 1 may be included in one or more layers of the hole injection layer, the hole transport layer, the electron blocking layer, the light emitting layer, the hole blocking layer, and the electron transport layer.

The organic light emitting device according to the present disclosure may be manufactured by materials and methods known in the art, except that one or more layers of the organic material layers include the compound of Chemical Formula 1. In addition, when the organic light emitting device includes a plurality of organic material layers, the organic material layers may be formed of the same material or different materials.

For example, the organic light emitting device according to the present disclosure can be manufactured by sequentially stacking a first electrode, an organic material layer and a second electrode on a substrate. In this case, the organic light emitting device may be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer and the electron transport layer thereon, and then depositing a material that can be used as the cathode thereon. In addition to such a method, the organic light emitting device may be manufactured by sequentially depositing a cathode material, an organic material layer and an anode material on a substrate.

In addition, the compound of Chemical Formula 1 may be formed into an organic material layer by a solution coating method as well as a vacuum deposition method at the time of manufacturing an organic light emitting device. Herein, the solution coating method means a spin coating, a dip coating, a doctor blading, an inkjet printing, a screen printing, a spray method, a roll coating, or the like, but is not limited thereto.

In addition to such a method, the organic light emitting device may be manufactured by sequentially depositing a cathode material, an organic material layer and an anode material on a substrate (International Publication WO2003/012890). However, the manufacturing method is not limited thereto.

As an example, the first electrode is an anode, and the second electrode is a cathode, or alternatively the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof, metal oxides such as zinc oxides, indium oxides, indium tin oxides (ITO), and indium zinc oxides (IZO); a combination of metals and oxides, such as ZnO:Al or $SnO_2$:Sb; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof, a multilayered structure material such as LiF/Al or $LiO_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to a electron injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer, and it is suitably a material having large mobility to the holes, which may receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The electron blocking layer is a layer provided between the hole transport layer and the light emitting layer in order to prevent the electrons injected in the cathode from being transferred to the hole transport layer without being recombined in the light emitting layer, which may also be referred to as an electron inhibition layer. The electron blocking layer is preferably a material having a smaller electron affinity than the electron transport layer.

The light emitting material is preferably a material which may receive holes and electrons transported from a hole transport layer and an electron transport layer, respectively, and combine the holes and the electrons to emit light in a visible ray region, and has good quantum efficiency to fluorescence or phosphorescence. Specific examples of the light emitting material include an 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene)(PPV)-based polymer; a spiro compound; polyfluorene, rubrene, and the like, but are not limited thereto.

The light emitting layer may include a host material and a dopant material. The host material may be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto. Preferably, the compound of Chemical Formula 1 can be included as a host material.

Examples of the dopant material include an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The hole blocking layer is a layer provided between the electron transport layer and the light emitting layer in order to prevent the holes injected in the anode from being transferred to the electron transport layer without being recombined in the light emitting layer, which may also be referred to as a hole inhibition layer or a hole blocking layer. The hole blocking layer is preferably a material having the large ionization energy.

The electron transport layer is a layer which receives electrons from an electron injection layer and transports the electrons to a light emitting layer, and an electron transport material is suitably a material which may receive electrons well from a cathode and transfer the electrons to a light emitting layer, and has a large mobility for electrons. Specific examples of the electron transport material include: an Al complex of 8-hydroxyquinoline; a complex including $Alq_3$; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples of the electron injection layer include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato) beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present disclosure may be a front side emission type, a back side emission type, or a double side emission type according to the used material.

In addition, the compound of Chemical Formula 1 may be included in an organic solar cell or an organic transistor in addition to an organic light emitting device.

The preparation of the compound of Chemical Formula 1 and the organic light emitting device containing the same will be described in detail in the following examples. However, these examples are presented for illustrative purposes only, and are not intended to limit the scope of the present disclosure.

PREPARATION EXAMPLE

Preparation Example 1: Preparation of Compound 1

Step 1) Preparation of Compound 1-a

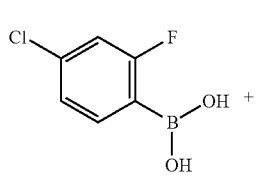

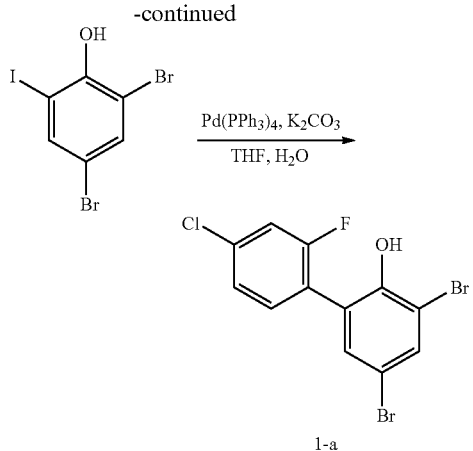

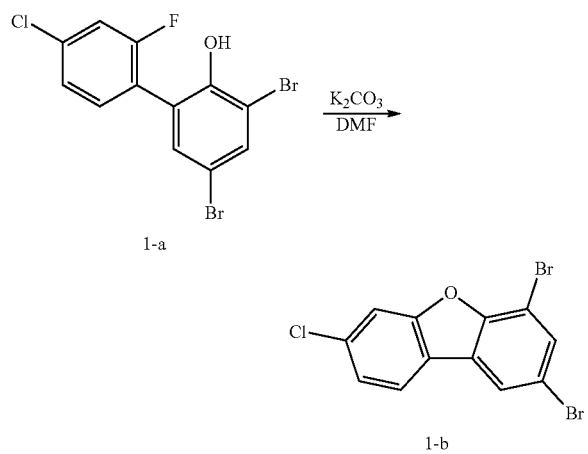

2,4-Dibromo-6-iodophenol (20 g, 52.9 mmol) and (4-chloro-2-fluorophenyl)boronic acid (9.2 g, 52.9 mmol) were added to 400 ml of tetrahydrofuran under a nitrogen atmosphere, and the mixture was stirred and refluxed. Then, potassium carbonate (21.9 g, 158.8 mmol) was dissolved in 22 ml of water, added thereto and sufficiently stirred, and then tetrakistriphenyl-phosphinopalladium (1.8 g, 1.6 mmol) was added. After the reaction for 1 hour, the reaction mixture was cooled to room temperature, the organic layer and the aqueous layer were separated, and the organic layer was distilled. This was added again to 403 ml of chloroform, dissolved and washed twice with water. The organic layer was then separated, anhydrous magnesium sulfate was added, stirred and then filtered. The filtrate was distilled under reduced pressure. The concentrated compound was purified by silica gel column chromatography to give a white solid compound 1-a (14.7 g, 73%, MS: [M+H]$^+$=381.4).

Step 2) Preparation of Compound 1-b

Compound 1-a (20 g, 52.6 mmol) was added to 400 ml of dimethylformamide under a nitrogen atmosphere, and the mixture was stirred and refluxed. Then, potassium carbonate (21.8 g, 157.7 mmol) was added, heated and stirred. After the reaction for 1 hour, the reaction mixture was cooled to room temperature, the organic layer was subjected to filtration treatment to remove a salt, and the filtered organic layer was distilled. This was added again to 189 ml of chloroform, dissolved and washed twice with water. The organic layer was then separated, anhydrous magnesium sulfate was added, stirred and then filtered. The filtrate was distilled under reduced pressure. The concentrated compound was recrystallized from chloroform and hexane to give a white solid compound 1-b (11.7 g, 62%, MS: [M+H]$^+$=361.4).

Step 3) Preparation of Compound 1-c

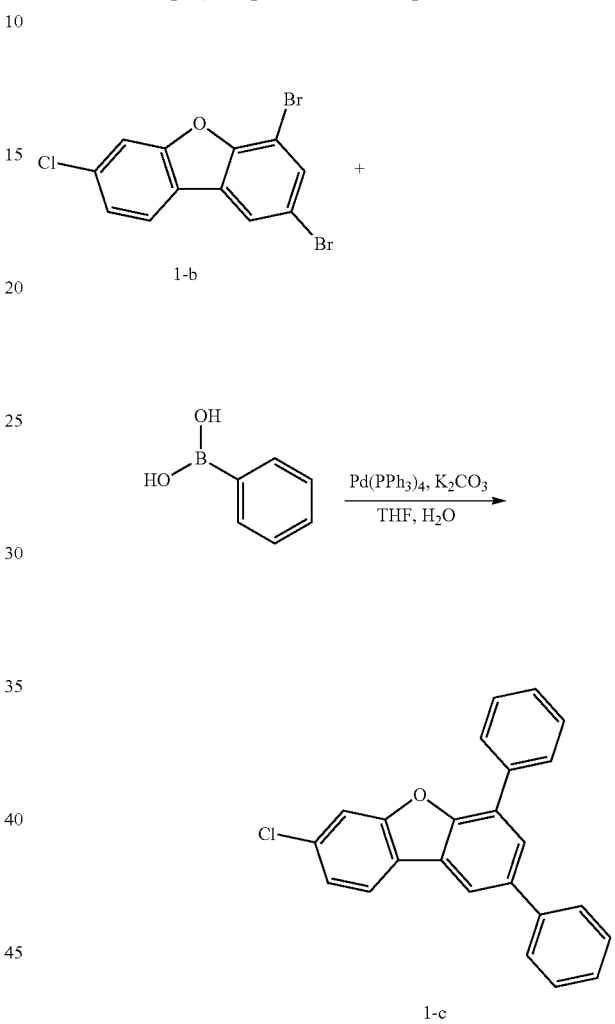

Compound 1-b (20 g, 55.5 mmol) and phenylboronic acid (14.2 g, 116.5 mmol) were added to 400 ml of tetrahydrofuran under a nitrogen atmosphere, and the mixture was stirred and refluxed. Then, potassium carbonate (23 g, 166.5 mmol) was dissolved in 23 ml of water, added thereto and sufficiently stirred, and then tetrakistriphenyl-phosphinopalladium (1.9 g, 1.7 mmol) was added. After the reaction for 1 hour, the reaction mixture was cooled to room temperature, the organic layer and the aqueous layer were separated, and then the organic layer was distilled. This was added again to 394 ml of chloroform, dissolved and washed twice with water. The organic layer was then separated, anhydrous magnesium sulfate was added, stirred and then filtered. The filtrate was distilled under reduced pressure. The concentrated compound was recrystallized from chloroform and ethanol to give a white solid compound 1-c (12 g, 61%, MS: [M+H]$^+$=355.8).

Step 4) Preparation of Compound 1-d

Step 5) Preparation of Compound 1

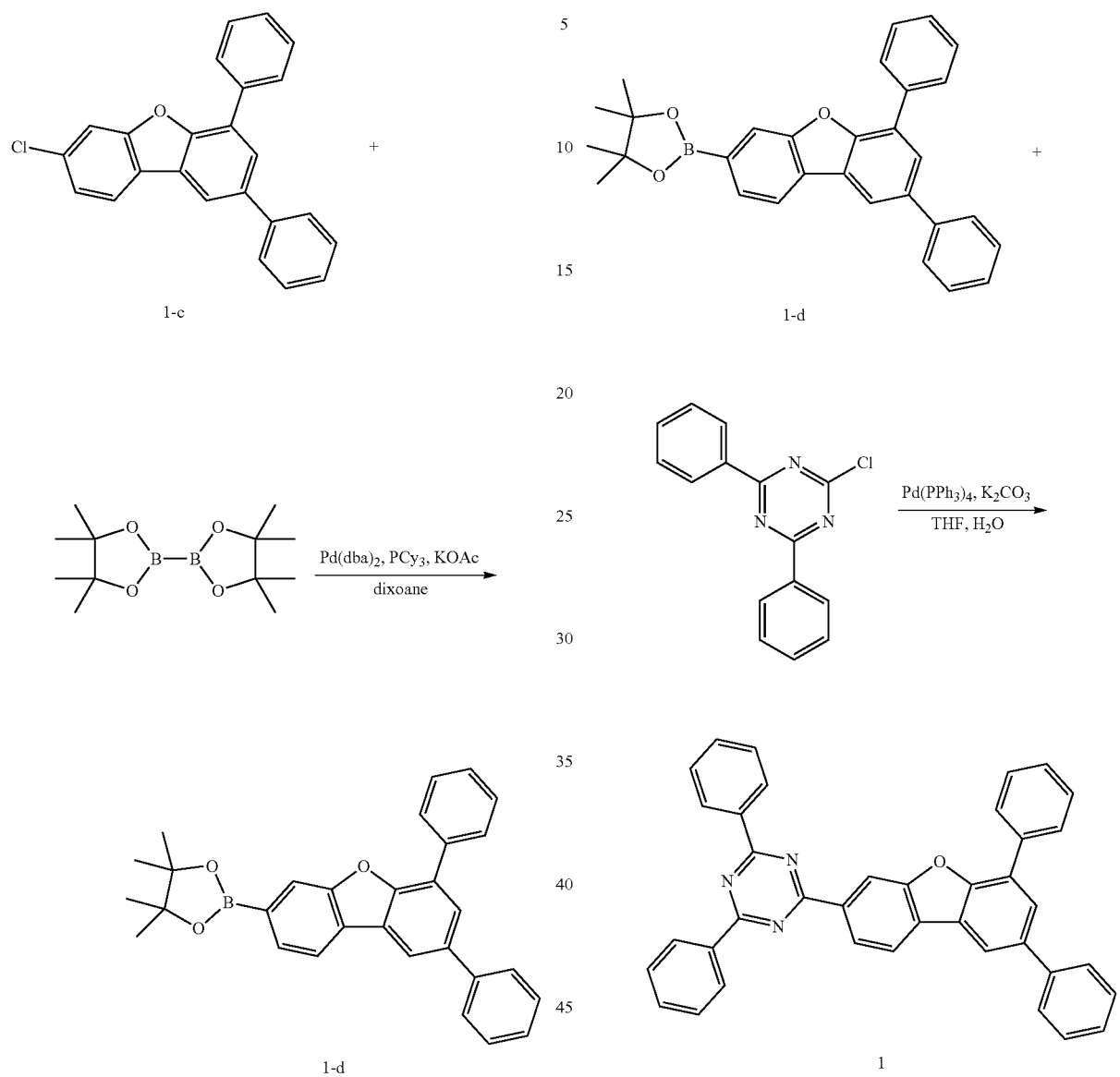

1-c 1-d 1-d

1

Compound 1-c (20 g, 56.4 mmol) and bis(pinacolato) diboron (14.3 g, 56.4 mmol) were added to 400 ml of dioxane under a nitrogen atmosphere, and the mixture was stirred and refluxed. Then, anhydrous potassium acetate (16.6 g, 169.1 mmol) was added thereto and sufficiently stirred, and then dibenzylidene acetone palladium (1 g, 1.7 mmol) and tricyclohexylphosphine (0.9 g, 3.4 mmol) were added. After the reaction for 7 hours, the reaction mixture was cooled to room temperature, the organic layer was subjected to filetration treatment to remove a salt, and then the filtered organic layer was distilled. This was added again to 252 ml of chloroform, dissolved and washed twice with water. The organic layer was separated, anhydrous magnesium sulfate was added, stirred and then filtered. The filtrate was distilled under reduced pressure. The concentrated compound was recrystallized from chloroform and ethanol to give a white solid compound 1-d (13.3 g, 53%, MS: [M+H]$^+$=447.4).

Compound 1-d (20 g, 44.8 mmol) and 2-chloro-4,6-diphenyl-1,3,5-triazine (13.2 g, 49.3 mmol) were added to 400 ml of tetrahydrofuran under a nitrogen atmosphere, and the mixture was stirred and refluxed. Then, potassium carbonate (18.6 g, 134.4 mmol) was dissolved in 19 ml of water, added thereto and sufficiently stirred, and then tetrakistriphenyl-phosphinopalladium (1.6 g, 1.3 mmol) was added. After the reaction for 2 hours, the reaction mixture was cooled to room temperature and then the produced solid was filtered. The solid was added to 494 ml (20 times the amount) of chloroform, dissolved and washed twice with water. The organic layer was then separated, anhydrous magnesium sulfate was added, stirred and then filtered. The filtrate was distilled under reduced pressure. The concentrated compound was recrystallized from chloroform and ethyl acetate to give a white solid compound 1 (19 g, 77%, MS: [M+H]$^+$=552.6).

Preparation Example 2: Preparation of Compound 2

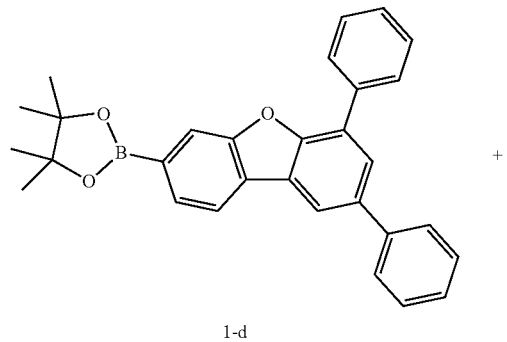

Preparation Example 3: Preparation of Compound 3

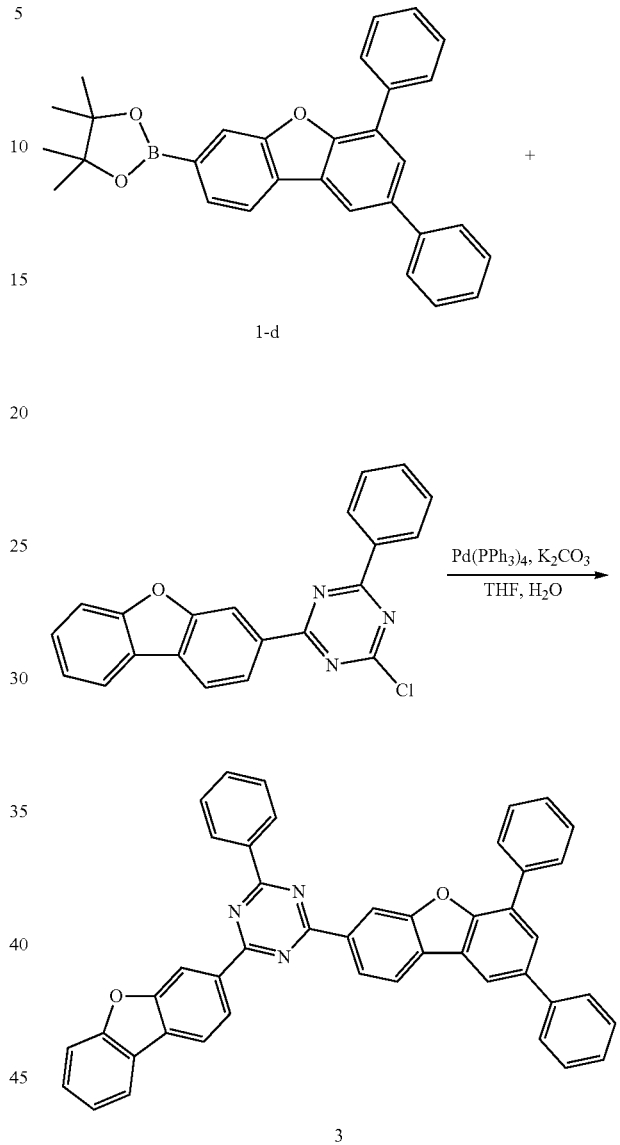

Compound 1-d (20 g, 44.8 mmol) and 2-chloro-4-(dibenzo[b,d]thiophen-4-yl)-6-phenyl-1,3,5-triazine (18.4 g, 49.3 mmol) were added to 400 ml of tetrahydrofuran under a nitrogen atmosphere, and the mixture was stirred and refluxed. Then, potassium carbonate (18.6 g, 134.4 mmol) was dissolved in 19 ml of water, added thereto and sufficiently stirred, and then tetrakistriphenyl-phosphinopalladium (1.6 g, 1.3 mmol) was added. After the reaction for 1 hour, the reaction mixture was cooled to room temperature and then the produced solid was filtered. The solid was added to 589 ml of chloroform, dissolved and washed twice with water. The organic layer was then separated, anhydrous magnesium sulfate was added, stirred and then filtered. The filtrate was distilled under reduced pressure. The concentrated compound was recrystallized from chloroform and ethyl acetate to give a white solid compound 2 (21.2 g, 72%, MS: $[M+H]^+=658.8$).

Compound 1-d (20 g, 44.8 mmol) and 2-chloro-4-(dibenzo[b,d]furan-4-yl)-6-phenyl-1,3,5-triazine (17.6 g, 49.3 mmol) were added to 400 ml of tetrahydrofuran under a nitrogen atmosphere, and the mixture was stirred and refluxed. Then, potassium carbonate (18.6 g, 134.4 mmol) was dissolved in 19 ml of water, added thereto and sufficiently stirred, and then tetrakistriphenyl-phosphinopalladium (1.6 g, 1.3 mmol) was added. After the reaction for 2 hours, the reaction mixture was cooled to room temperature and then the produced solid was filtered. The solid was added to 575 ml of chloroform, dissolved and washed twice with water. The organic layer was then separated, anhydrous magnesium sulfate was added, stirred and then filtered. The filtrate was distilled under reduced pressure. The concentrated compound was recrystallized from chloroform and ethyl acetate to give a white solid compound 3 (22.1 g, 77%, MS: $[M+H]^+=642.7$).

Preparation Example 4: Preparation of Compound 4

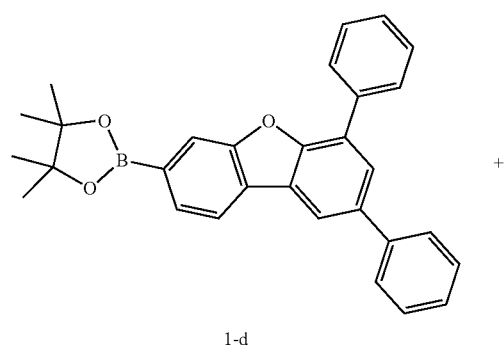

Preparation Example 5: Preparation of Compound 5

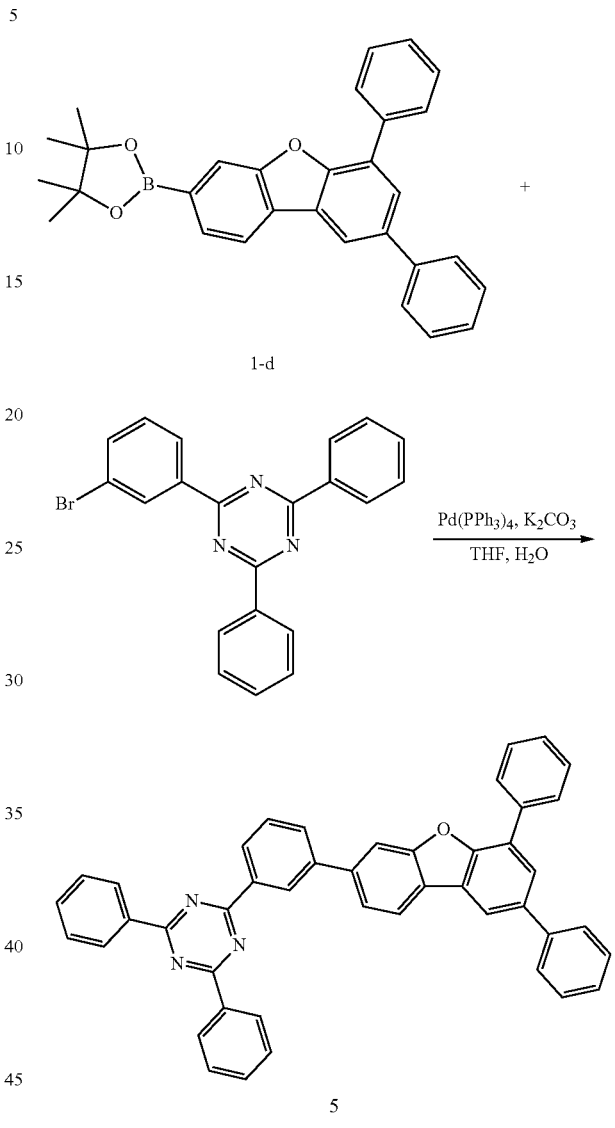

Compound 1-d (20 g, 44.8 mmol) and 2-(4-chloro-6-phenyl-1,3,5-triazin-2-yl)-9-phenyl-9H-carbazole (21.3 g, 49.3 mmol) were added to 400 ml of tetrahydrofuran under a nitrogen atmosphere, and the mixture was stirred and refluxed. Then, potassium carbonate (18.6 g, 134.4 mmol) was dissolved in 19 ml of water, added thereto and sufficiently stirred, and then tetrakistriphenyl-phosphinopalladium (1.6 g, 1.3 mmol) was added. After the reaction for 2 hours, the reaction mixture was cooled to room temperature and then the produced solid was filtered. The solid was added to 642 ml of chloroform, dissolved and washed twice with water. The organic layer was then separated, anhydrous magnesium sulfate was added, stirred and then filtered. The filtrate was distilled under reduced pressure. The concentrated compound was recrystallized from chloroform and ethyl acetate to give a yellow solid compound 4 (19.3 g, 60%, MS: [M+H]$^+$=717.8).

Compound 1-d (20 g, 44.8 mmol) and 2-(3-bromophenyl)-4,6-diphenyl-1,3,5-triazine (19.1 g, 49.3 mmol) were added to 400 ml of tetrahydrofuran under a nitrogen atmosphere, and the mixture was stirred and refluxed. Then, potassium carbonate (18.6 g, 134.4 mmol) was dissolved in 19 ml of water, added thereto and sufficiently stirred, and then tetrakistriphenyl-phosphinopalladium (1.6 g, 1.3 mmol) was added. After the reaction for 3 hours, the reaction mixture was cooled to room temperature and then the produced solid was filtered. The solid was added to 563 ml of chloroform, dissolved and washed twice with water. The organic layer was then separated, anhydrous magnesium sulfate was added, stirred and then filtered. The filtrate was distilled under reduced pressure. The concentrated compound was recrystallized from chloroform and ethyl acetate to give a yellow solid compound 5 (18.3 g, 65%, MS: [M+H]$^+$=628.7).

Preparation Example 6: Preparation of Compound 6

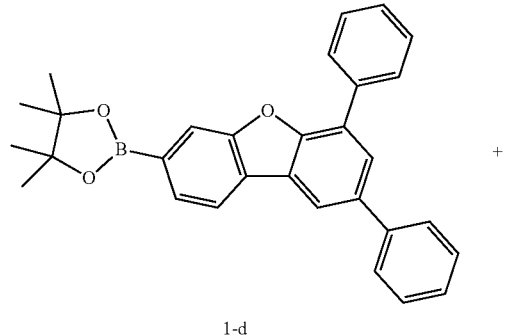

1-d

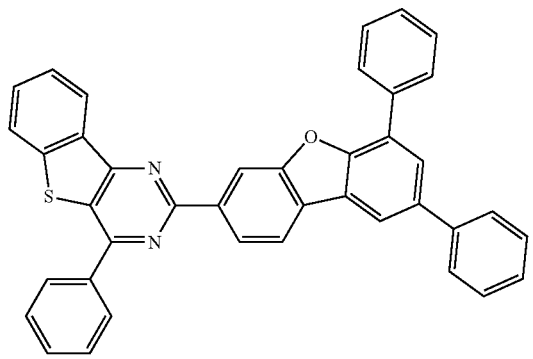

6

Compound 1-d (20 g, 44.8 mmol) and 2-chloro-4-phenylbenzo[4,5]thieno[3,2-d]pyrimidine (14.6 g, 49.3 mmol) were added to 400 ml of tetrahydrofuran under a nitrogen atmosphere, and the mixture was stirred and refluxed. Then, potassium carbonate (18.6 g, 134.4 mmol) was dissolved in 19 ml of water, added thereto and sufficiently stirred, and then tetrakistriphenyl-phosphinopalladium (1.6 g, 1.3 mmol) was added. After the reaction for 1 hour, the reaction mixture was cooled to room temperature and then the produced solid was filtered. The solid was added to 520 ml of chloroform, dissolved and washed twice with water. The organic layer was then separated, anhydrous magnesium sulfate was added, stirred and then filtered. The filtrate was distilled under reduced pressure. The concentrated compound was recrystallized from chloroform and ethyl acetate to give a white solid compound 6 (19.3 g, 74%, MS: [M+H]$^+$=581.7).

Preparation Example 7: Preparation of Compound 7

Step 1) Preparation of Compound 7-a

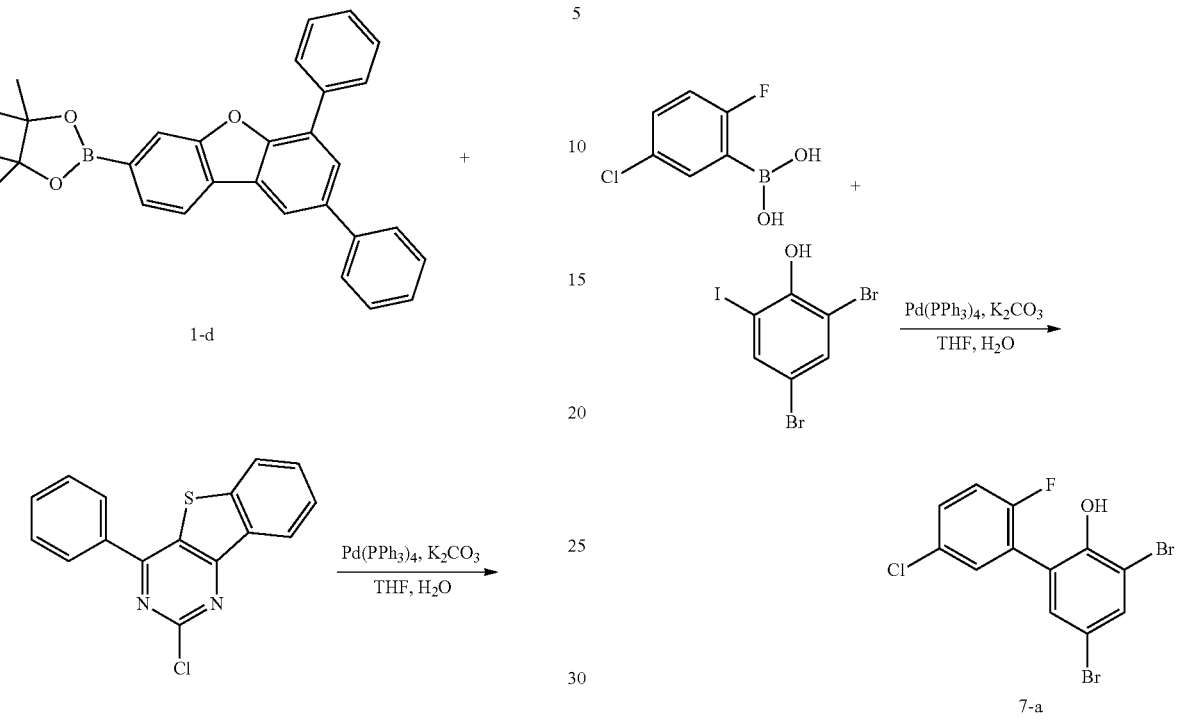

7-a 2,4-dibromo-6-iodophenol (20 g, 52.9 mmol) and (5-chloro-2-fluorophenyl)boronic acid (10.2 g, 58.2 mmol) were added to 400 ml of tetrahydrofuran under a nitrogen atmosphere, and the mixture was stirred and refluxed. Then, potassium carbonate (21.9 g, 158.8 mmol) was dissolved in 22 ml of water, added thereto and sufficiently stirred, and then tetrakistriphenyl-phosphinopalladium (1.8 g, 1.6 mmol) was added. After the reaction for 1 hour, the reaction mixture was cooled to room temperature and then the organic layer and the aqueous layer were separated, and the organic layer was distilled. This was added again to 403 ml of chloroform, dissolved and washed twice with water. The organic layer was separated, anhydrous magnesium sulfate was added, stirred and then filtered. The filtrate was distilled under reduced pressure. The concentrated compound was purified by silica gel column chromatography to give a white solid compound 7-a (10.5 g, 52%, MS: [M+H]$^+$=381.4).

Step 2) Preparation of Compound 7-b

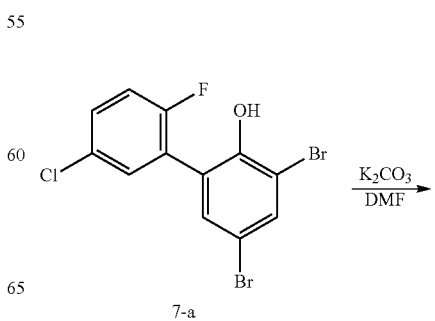

7-a

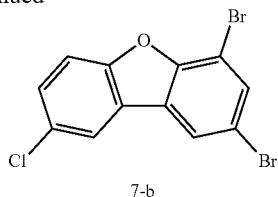

7-b

Compound 7-a (20 g, 52.6 mmol) was added to 400 ml of dimethylformamide under a nitrogen atmosphere, and the mixture was stirred and refluxed. Then, potassium carbonate (21.8 g, 157.7 mmol) was added, heated and stirred. After the reaction for 1 hour, the reaction mixture was cooled to room temperature and then the organic layer was subjected to filtration treatment to remove a salt, and then the filtered organic layer was distilled. This was added again to 189 ml of chloroform, dissolved and washed twice with water. The organic layer was separated, anhydrous magnesium sulfate was added, stirred and then filtered. The filtrate was distilled under reduced pressure. The concentrated compound was recrystallized from chloroform and hexane to give a white solid compound 7-b (12.7 g, 67%, MS: $[M+H]^+=361.4$).

Step 3) Preparation of Compound 7-c

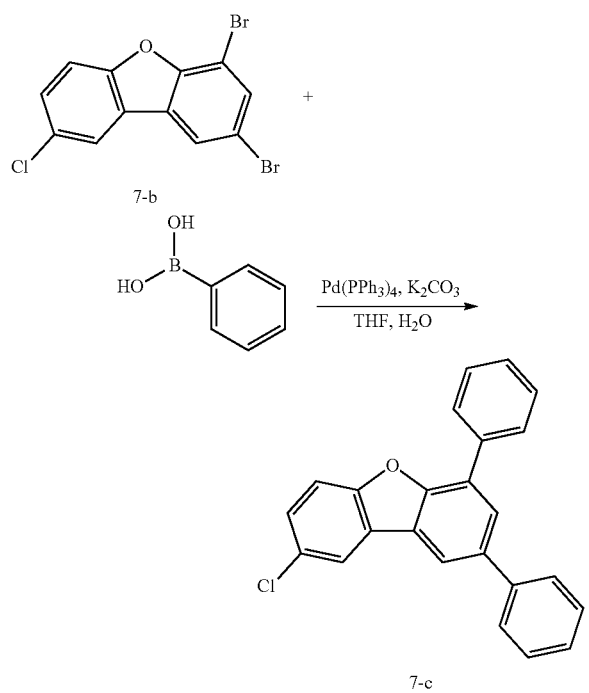

Compound 7-b (20 g, 55.5 mmol) and phenylboronic acid (14.2 g, 116.5 mmol) were added to 400 ml of tetrahydrofuran under a nitrogen atmosphere, and the mixture was stirred and refluxed. Then, potassium carbonate (23 g, 166.5 mmol) was dissolved in 23 ml of water, added thereto and sufficiently stirred, and then tetrakistriphenyl-phosphinopalladium (1.9 g, 1.7 mmol) was added. After the reaction for 2 hours, the reaction mixture was cooled to room temperature and then the organic layer and the aqueous layer were separated, and the organic layer was distilled. This was added again to 394 ml of chloroform, dissolved and washed twice with water. The organic layer was then separated, anhydrous magnesium sulfate was added, stirred and then filtered. The filtrate was distilled under reduced pressure. The concentrated compound was recrystallized from chloroform and ethanol to give a white solid compound 7-c (14 g, 71%, MS: $[M+H]^+=355.8$).

Step 4) Preparation of Compound 7-d

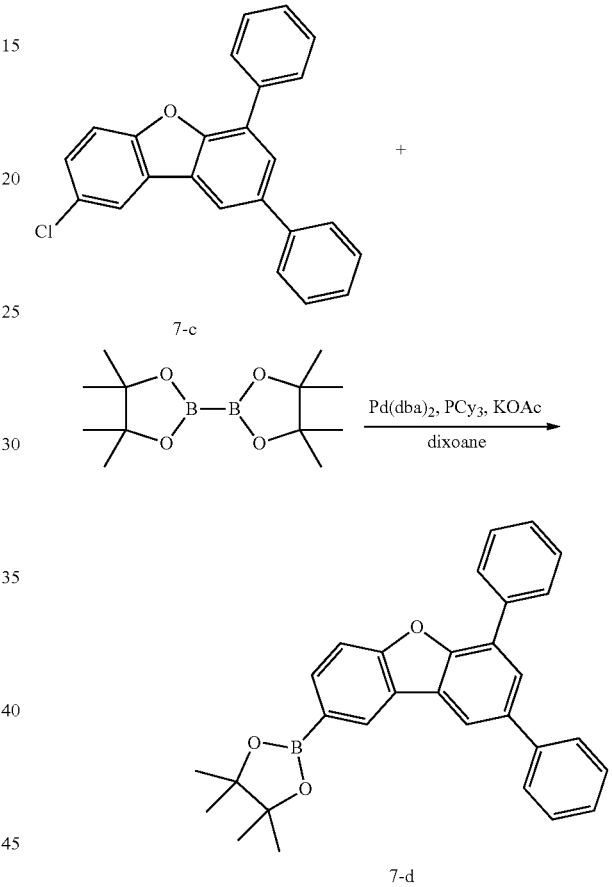

Compound 7-c (20 g, 56.4 mmol) and bis(pinacolato)diboron (14.3 g, 56.4 mmol) were added to 400 ml of dioxane under a nitrogen atmosphere, and the mixture was stirred and refluxed. Then, anhydrous potassium acetate (16.6 g, 169.1 mmol) was added thereto and sufficiently stirred, and then dibenzylidene acetone palladium (1 g, 1.7 mmol) and tricyclohexylphosphine (0.9 g, 3.4 mmol) were added. After the reaction for 4 hours, the reaction mixture was cooled to room temperature and then the organic layer was subjected to filtration treatment to remove a salt, and then the filtered organic layer was distilled. This was added again to 252 ml of chloroform, dissolved and washed twice with water. The organic layer was separated, anhydrous magnesium sulfate was added, stirred and then filtered. The filtrate was distilled under reduced pressure. The concentrated compound was recrystallized from chloroform and ethanol to give a white solid compound 7-d (16.6 g, 66%, MS: $[M+H]^+=447.4$).

Step 5) Preparation of Compound 7

Preparation Example 8: Preparation of Compound 8

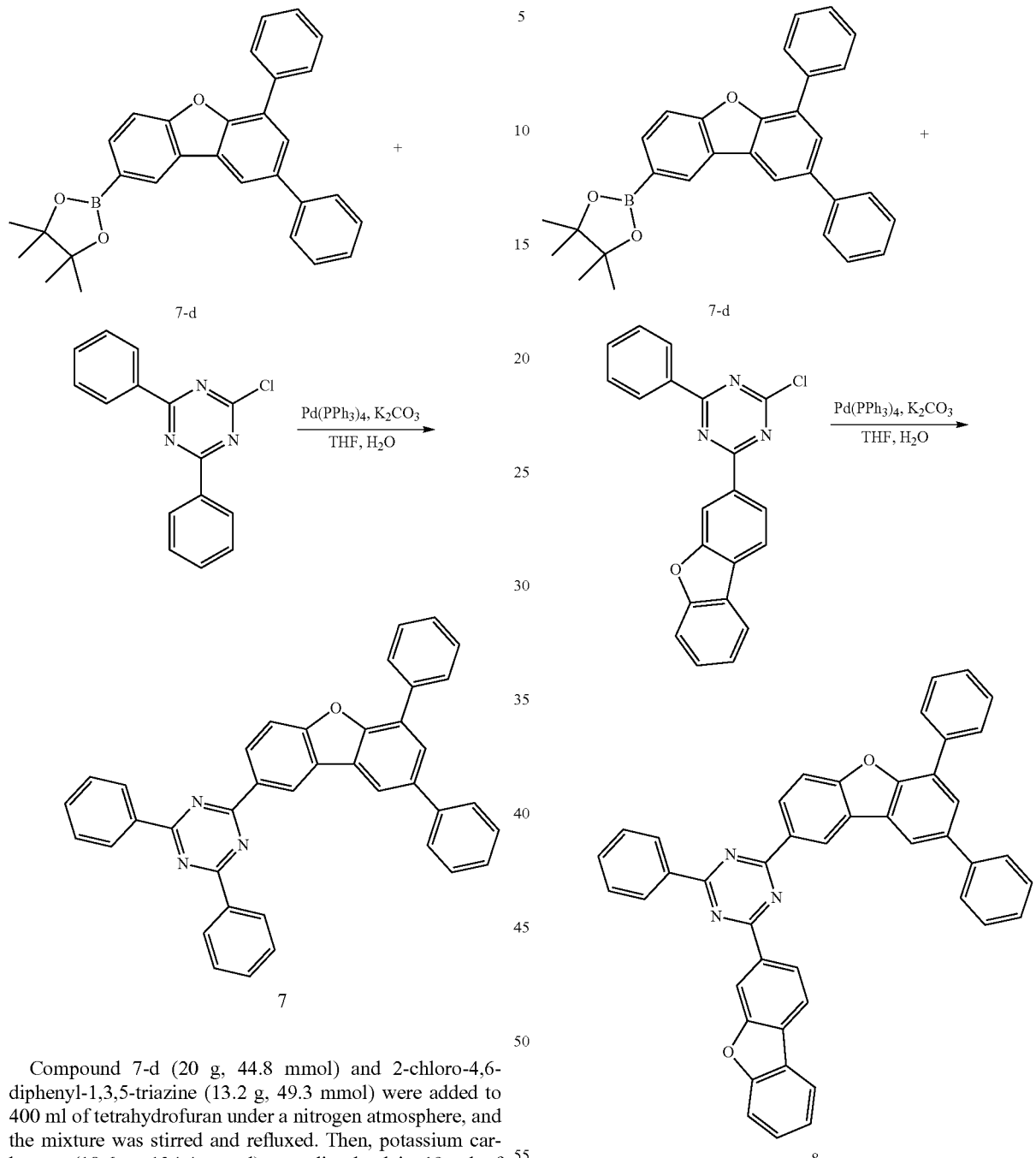

Compound 7-d (20 g, 44.8 mmol) and 2-chloro-4,6-diphenyl-1,3,5-triazine (13.2 g, 49.3 mmol) were added to 400 ml of tetrahydrofuran under a nitrogen atmosphere, and the mixture was stirred and refluxed. Then, potassium carbonate (18.6 g, 134.4 mmol) was dissolved in 19 ml of water, added thereto and sufficiently stirred, and then tetrakistriphenyl-phosphinopalladium (1.6 g, 1.3 mmol) was added. After the reaction for 2 hours, the reaction mixture was cooled to room temperature and then the produced solid was filtered. The solid was added to 494 ml of chloroform, dissolved and washed twice with water. The organic layer was then separated, anhydrous magnesium sulfate was added, stirred and then filtered. The filtrate was distilled under reduced pressure. The concentrated compound was recrystallized from chloroform and ethyl acetate to give a white solid compound 7 (18.3 g, 74%, MS: [M+H]$^+$=552.6).

Compound 7-d (20 g, 44.8 mmol) and 2-chloro-4-(dibenzo[b,d]furan-3-yl)-6-phenyl-1,3,5-triazine (17.6 g, 49.3 mmol) were added to 400 ml of tetrahydrofuran under a nitrogen atmosphere, and the mixture was stirred and refluxed. Then, potassium carbonate (18.6 g, 134.4 mmol) was dissolved in 19 ml of water, added thereto and sufficiently stirred, and then tetrakistriphenyl-phosphinopalladium (1.6 g, 1.3 mmol) was added. After the reaction for 3 hours, the reaction mixture was cooled to room temperature and then the produced solid was filtered. The solid was added to 575 ml of chloroform, dissolved and washed twice with water. The organic layer was then separated, anhydrous magnesium sulfate was added, stirred and then filtered. The filtrate was distilled under reduced pressure. The concentrated compound was recrystallized from chloroform and ethyl acetate to give a white solid compound 8 (14.4 g, 50%, MS: $[M+H]^+$=642.7).

EXAMPLE

Example 1

A glass substrate on which ITO (indium tin oxide) was coated as a thin film to a thickness of 1400 Å was put into distilled water in which a detergent was dissolved, and ultrasonically cleaned. At this time, a product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, dried, and then transferred to a plasma cleaner. In addition, the substrate was cleaned for 5 minutes using oxygen plasma and then transferred to a vacuum depositor.

On the ITO transparent electrode thus prepared, a compound HT-A below and a compound PD below were thermally vacuum-deposited in a ratio of 95:5 to a thickness of 100 Å, and then only a compound HT-A below was deposited to a thickness of 1150 Å to form a hole transport layer. A compound HT-B below was thermally vacuum-deposited to a thickness of 450 Å on the hole transport layer to form an electronic blocking layer. Then, the compound 1 previously prepared and a compound GD below was vacuum-deposited in a ratio of 85:15 to a thickness of 400 Å on the electronic blocking layer to form a light emitting layer. A compound ET-A below was vacuum-deposited to a thickness of 50 Å on the light emitting layer to form a hole blocking layer. A compound ET-B below and a compound Liq below were thermally vacuum-deposited in a ratio of 2:1 to a thickness of 250 Å on the hole blocking layer, and then LiF and magnesium were vacuum-deposited in a ratio of 1:1 to a thickness of 30 Å to form an electron transport and injection layer. Magnesium and silver were deposited in a ratio of 1:4 to a thickness of 160 Å on the electron injection layer to form a cathode, thereby completing the manufacture of an organic light emitting device.

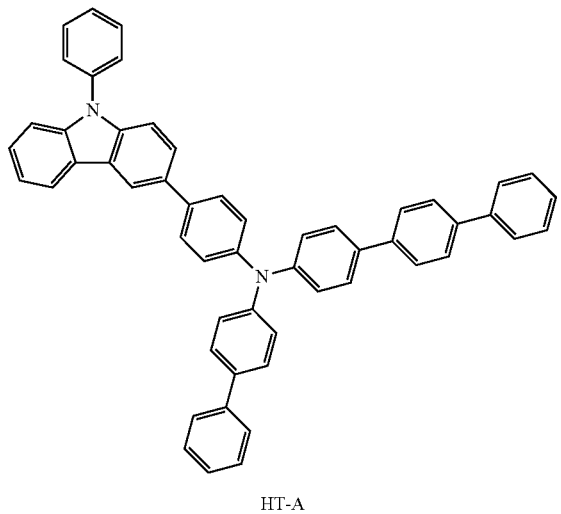

HT-A

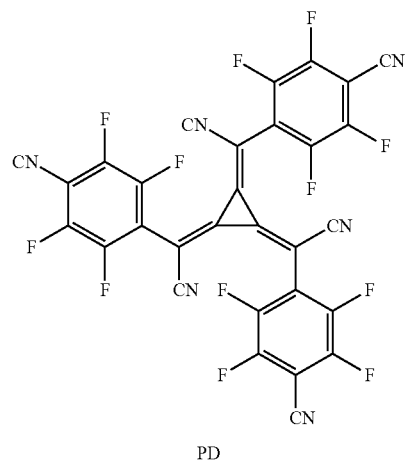

PD

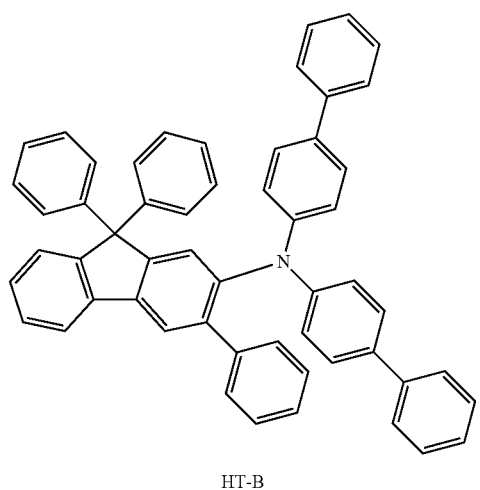

HT-B

-continued

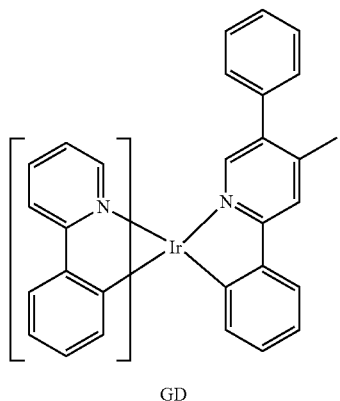

GD

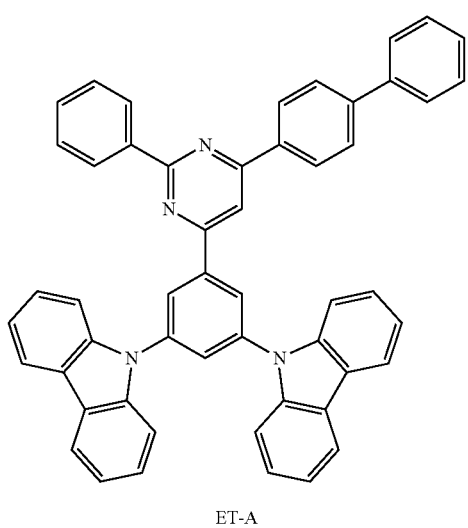

ET-A

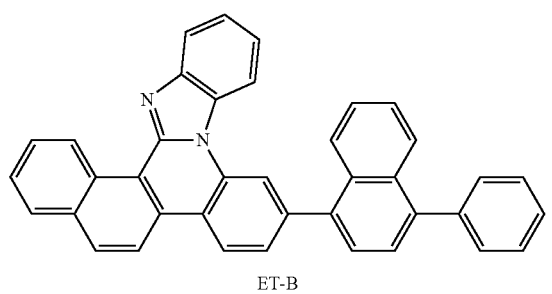

ET-B

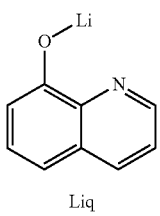

Liq

In the above-mentioned process, the vapor deposition rate of the organic material was maintained at 0.4 to 0.7 Å/sec, the deposition rate of lithium fluoride of the cathode was maintained at 0.3 Å/sec, the deposition rate of silver and magnesium was maintained at 2 Å/sec, and the degree of vacuum during the deposition was maintained at $2 \times 10^{-7}$ to $5 \times 10^{-6}$ torr, thereby manufacturing an organic light emitting device.

Examples 2 to 8

The organic light emitting devices were manufactured in the same manner as in Example 1, except that the compounds shown in Table 1 below were used instead of the compound 1.

Comparative Examples 1 to 4

The organic light emitting devices were manufactured in the same manner as in Example 1, except that the compounds shown in Table 1 below were used instead of the compound 1. In Table 1, the compounds GH-A, GH-B, GH-C and GH-D in Table 1 are as follows.

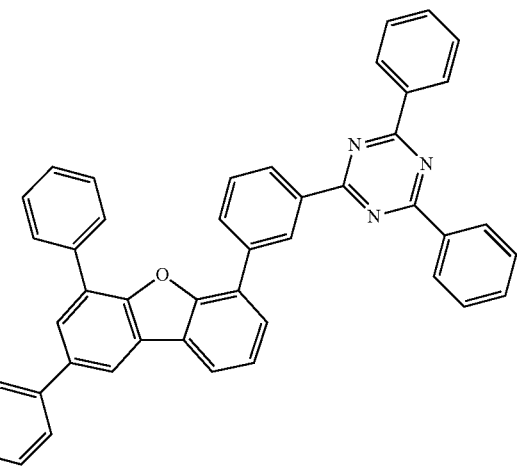

GH-A

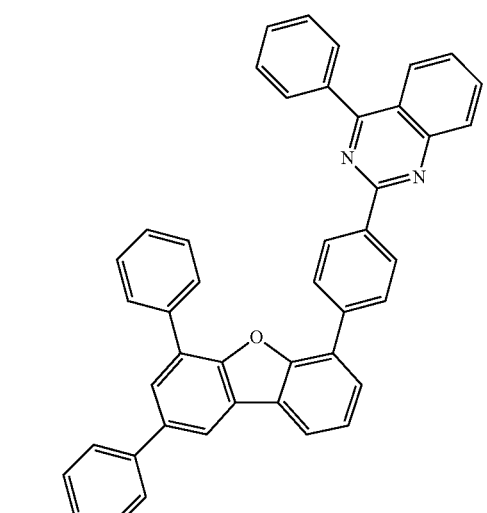

GH-B

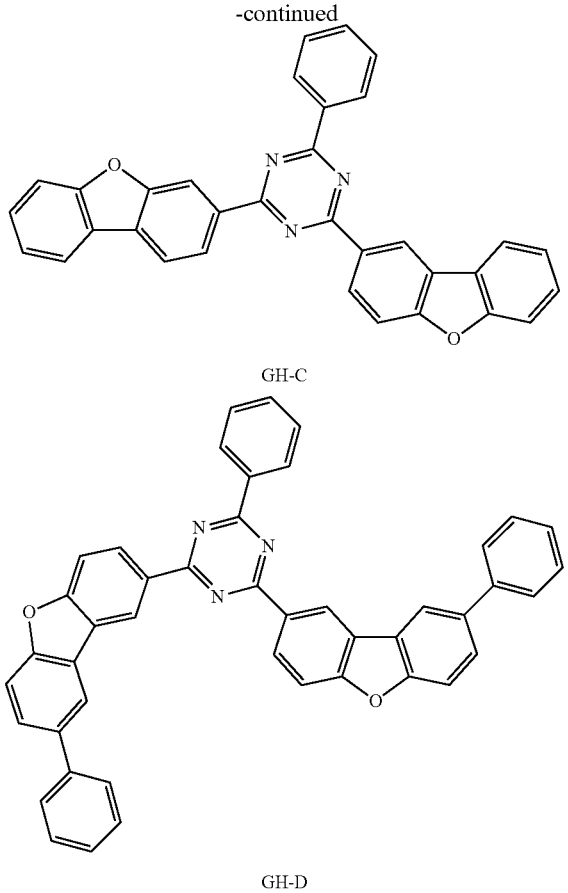

GH-C

GH-D

Experimental Example

The voltage, efficiency and lifetime (T95) were measured by applying a current to the organic light emitting devices manufactured in Examples and Comparative Examples, and the results are shown in Table 1 below. At this time, the voltage and efficiency were measured by applying a current density of 10 mA/cm². Further, T95 in Table 1 means the time required for the luminance to be reduced to 95% of the initial luminance at a current density of 20 mA/cm².

TABLE 1

|  | Light emitting layer (host) | Voltage (V) | Efficiency (cd/A) | Lifetime (T95, hr) |
| --- | --- | --- | --- | --- |
| Example 1 | Compound 1 | 4.7 | 37.5 | 92 |
| Example 2 | Compound 2 | 4.9 | 39.3 | 77 |
| Example 3 | Compound 3 | 4.6 | 37.4 | 95 |
| Example 4 | Compound 4 | 4.5 | 38 | 95 |
| Example 5 | Compound 5 | 4.6 | 39.5 | 93 |
| Example 6 | Compound 6 | 4.9 | 38.3 | 81 |
| Example 7 | Compound 7 | 5.1 | 38.5 | 90 |
| Example 8 | Compound 8 | 4.7 | 37.3 | 88 |
| Comparative Example 1 | GH-A | 5.6 | 35 | 51 |
| Comparative Example 2 | GH-B | 5.4 | 33 | 56 |
| Comparative Example 3 | GH-C | 5.6 | 25 | 59 |
| Comparative Example 4 | GH-D | 5.2 | 30.4 | 65 |

As shown in Table 1 above, it was confirmed that the organic light emitting device including a compound according to one embodiment of the present disclosure exhibits low voltage, high efficiency and long lifetime characteristics, as compared with the organic light emitting device including a comparative compound having a similar structure. In particular, when comparing Example 5 including Compound 5 with Comparative Examples 1 and 2 including the compounds GH-A and GH-B, it is presumed that whether or not the steric hindrance according to the substitution position of the N-containing substituent of dibenzofuran has been eliminated greatly contributes to the molecular stability. In addition, when comparing Examples of one embodiment and Comparative Examples 3 and 4 containing the compounds GH-C and GH-D, it is expected that in the case of the compound of one embodiment, the electron stability is increased through additional bonds between intramolecular orbitals.

EXPLANATION OF SYMBOLS

1: substrate 2: anode
3: light emitting layer 4: cathode
5: hole injection layer
6: hole transport layer
7: electron transport layer
8: electron injection layer
9: electron blocking layer
10: hole blocking layer

The invention claimed is:
1. A compound of the following Chemical Formula 1:

Chemical Formula 1

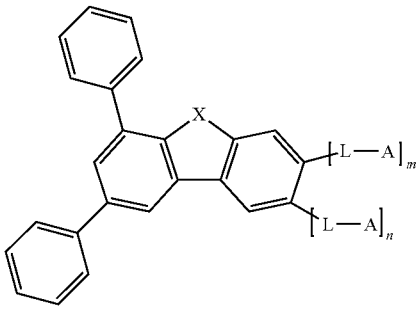

wherein, in Chemical Formula 1,
m and n are each independently 0 or 1, with the proviso that at least one of m and n is 1,
X is O or S,
L is a single bond or phenylene,
A is any one selected from the group consisting of the following:

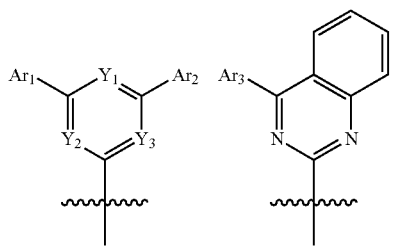

-continued

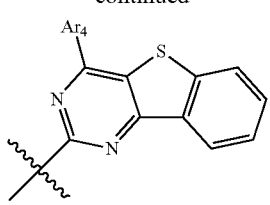

Y₁ to Y₃ are each independently N or CH, with the proviso that at least two of Y₁ to Y₃ are N, and Ar₁ to Ar₄ are each independently a substituted or unsubstituted $C_{6-60}$ aryl; or a substituted or unsubstituted $C_{2-60}$ heteroaryl containing any one or more selected from the group consisting of N, O and S.

2. The compound of claim 1, wherein the compound is of the following Chemical Formula 1-1 or 1-2:

Chemical Formula 1-1

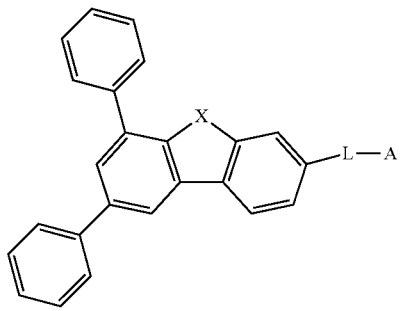

Chemical Formula 1-2

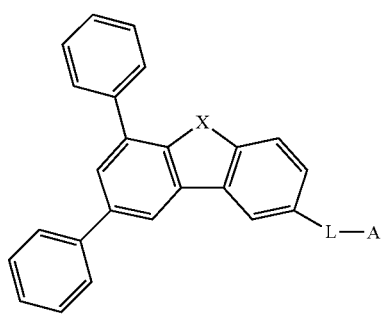

wherein, in Chemical Formula 1-1 or 1-2,

X, L and A are the same as defined in claim 1.

3. The compound of claim 1, wherein Ar₁ to Ar₄ are each independently phenyl, biphenylyl, dibenzofuranyl, dibenzothiophenyl, phenyl carbazolyl, or carbazolyl phenyl.

4. The compound of claim 1, wherein at least one of Ar₁ and Ar₂ is a substituted or unsubstituted $C_{6-60}$ aryl.

5. The compound of claim 1, wherein the compound of Chemical Formula 1 is any one selected from the group consisting of the following:

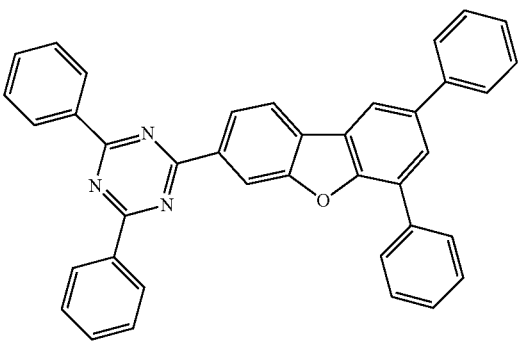

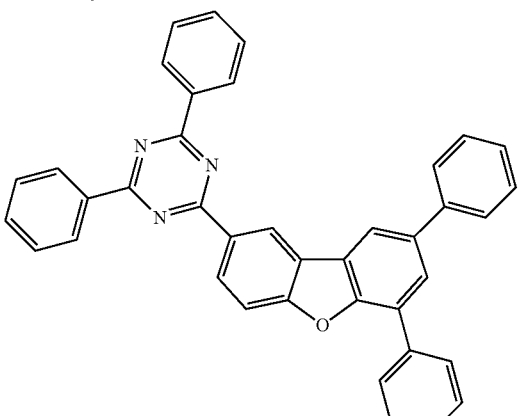

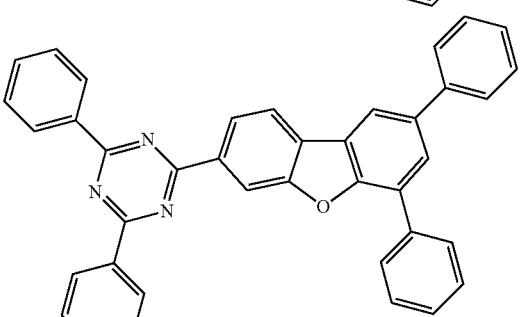

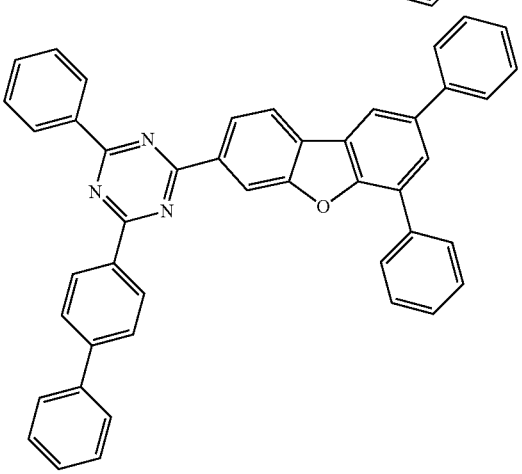

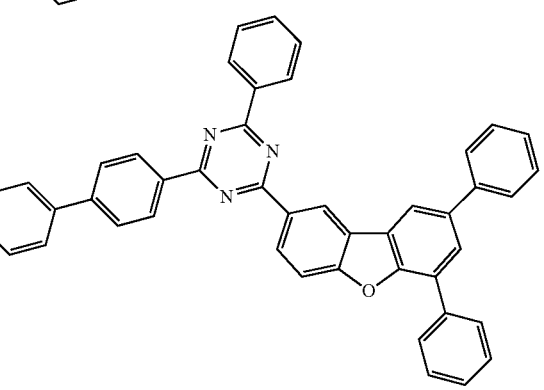

57
-continued
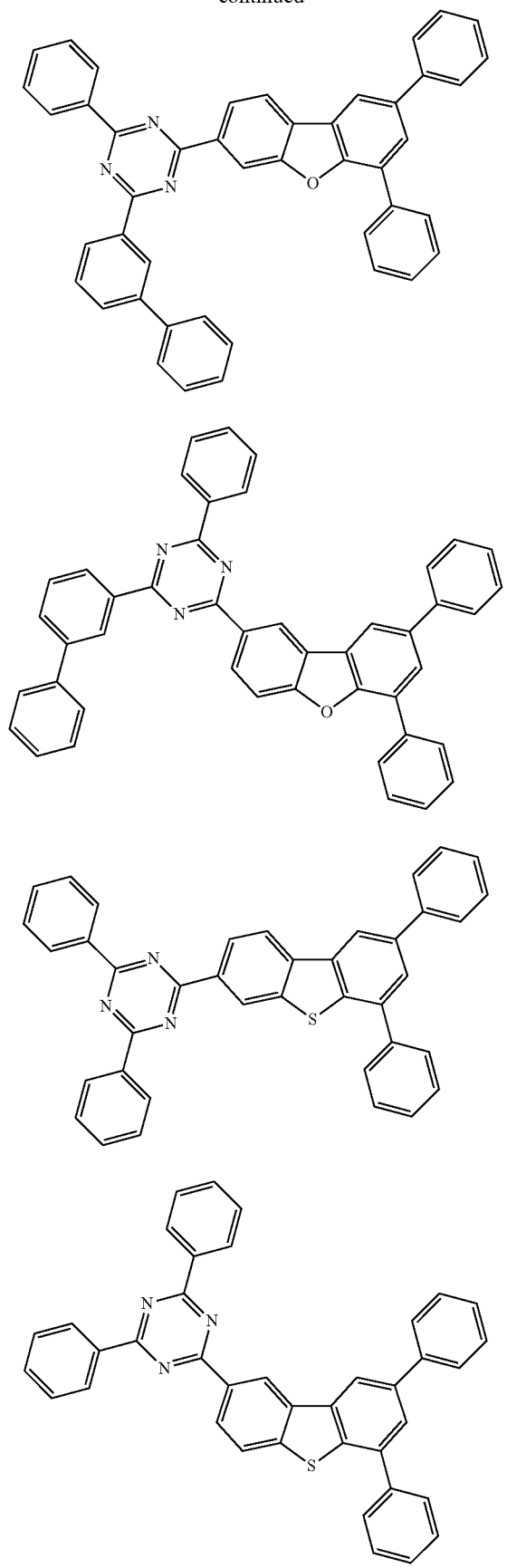
58
-continued
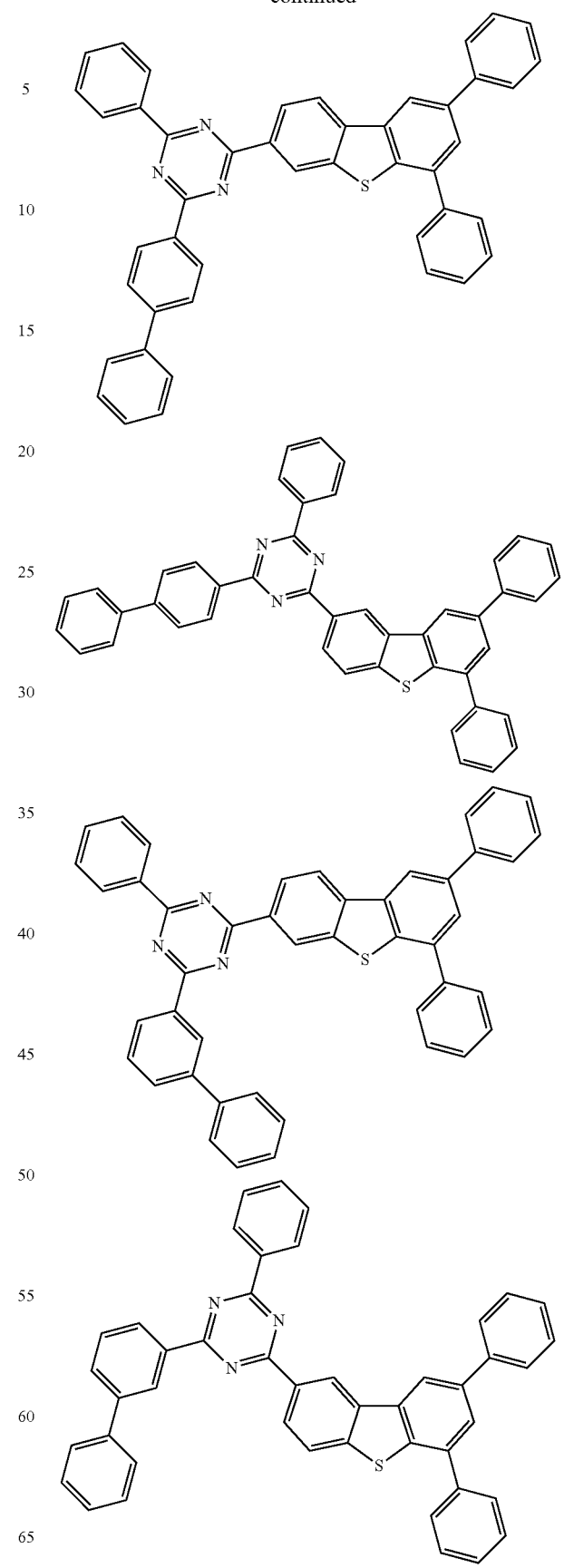

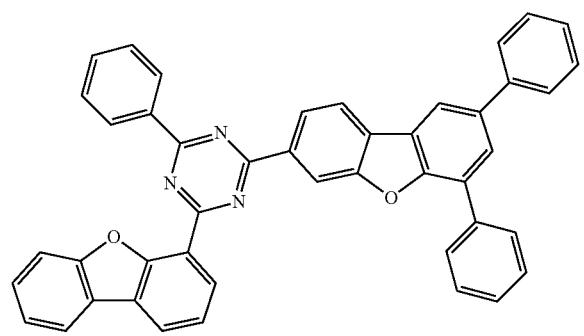
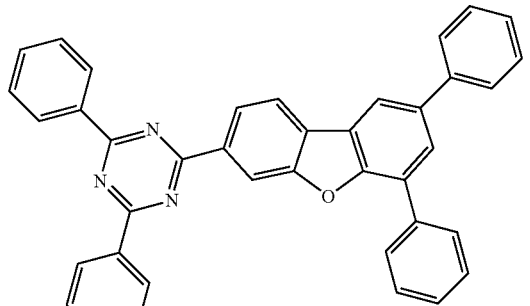
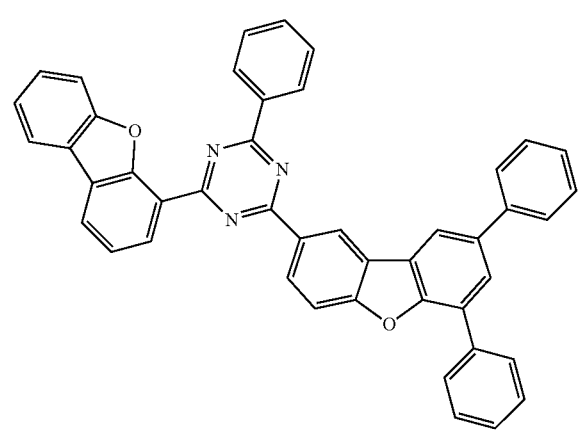
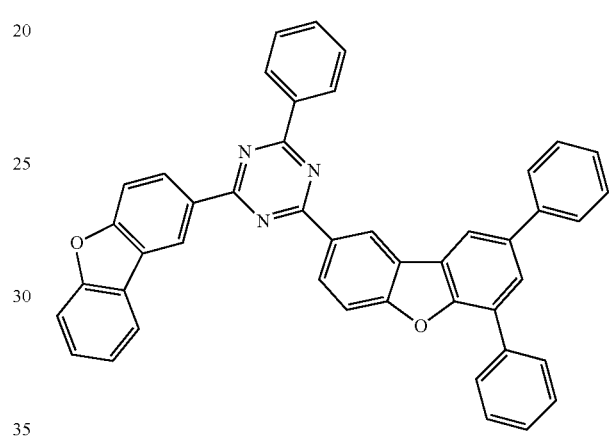
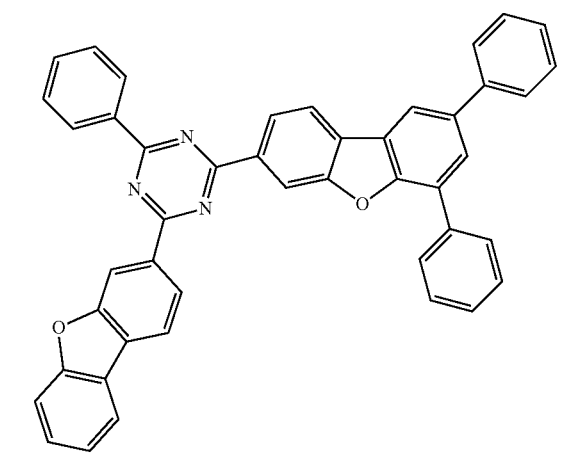
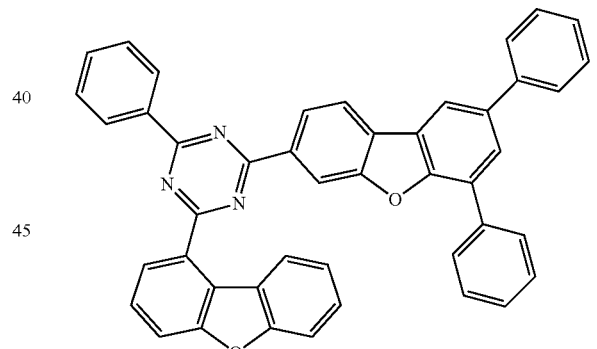
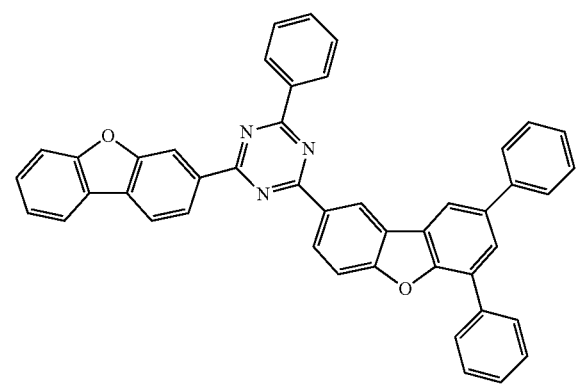
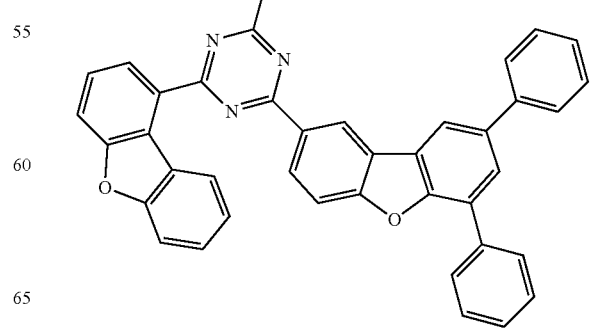

61
-continued
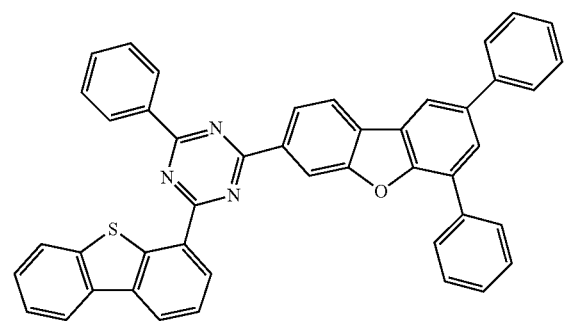
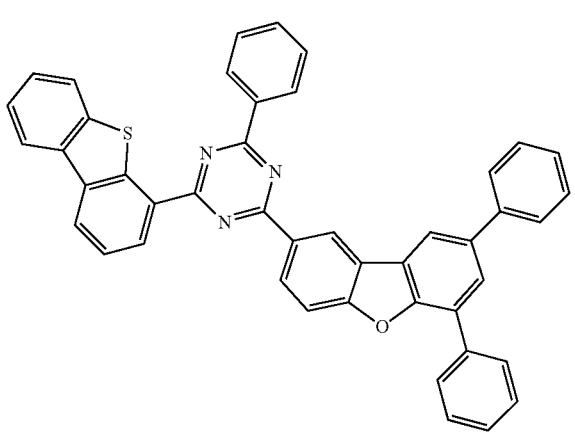
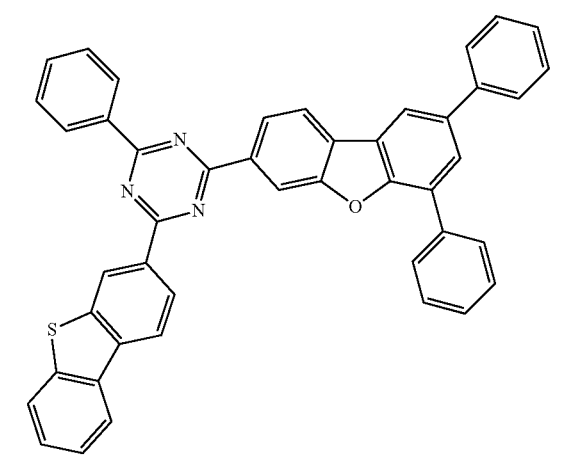
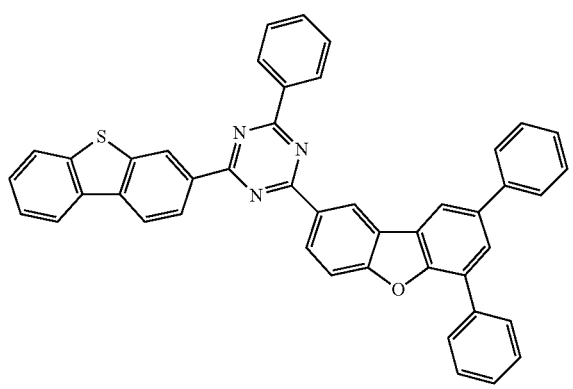
62
-continued
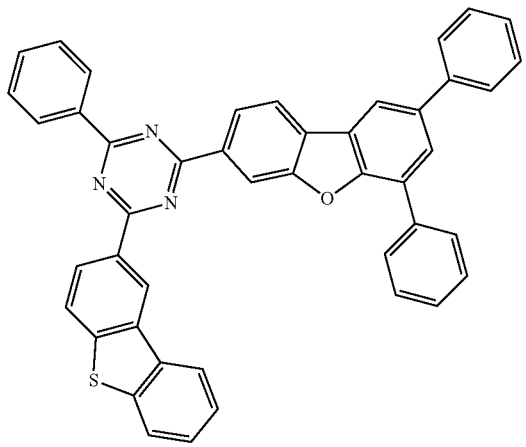
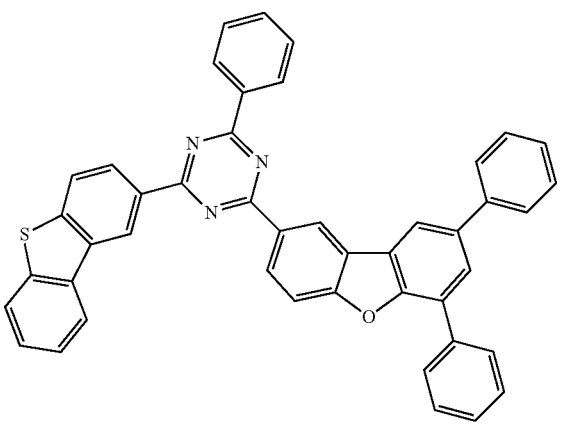
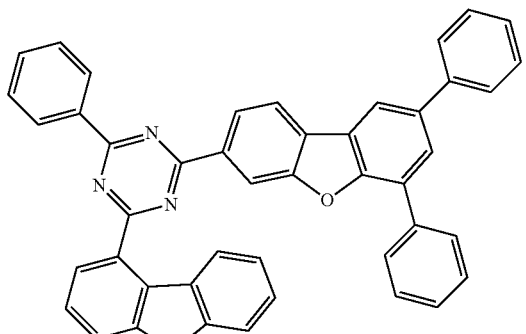
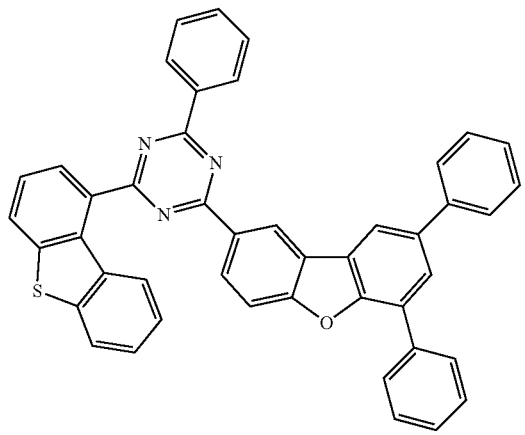

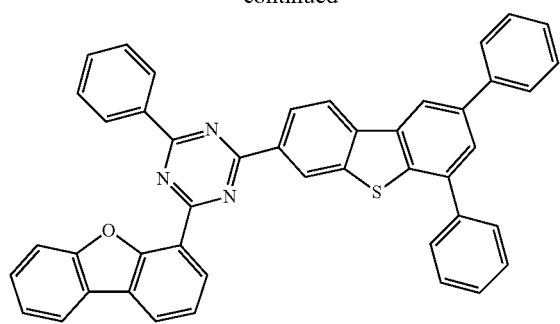
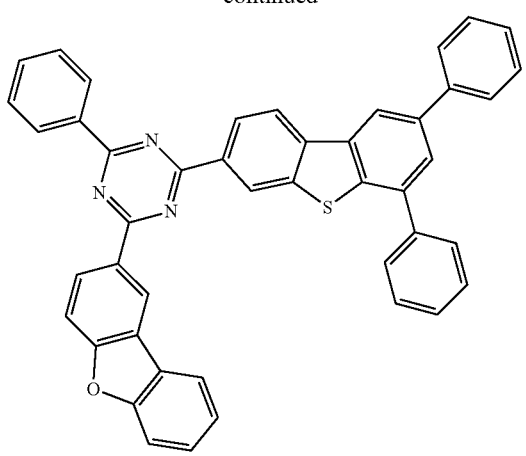
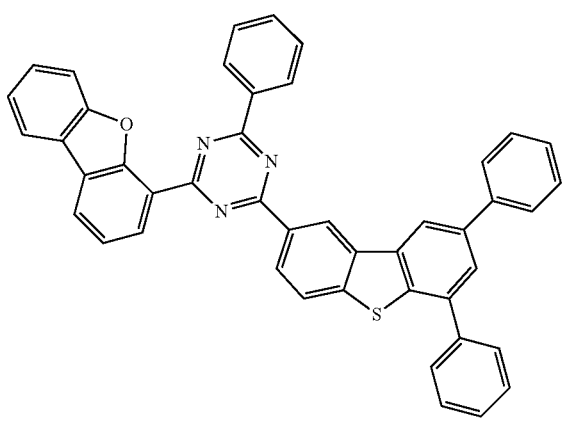
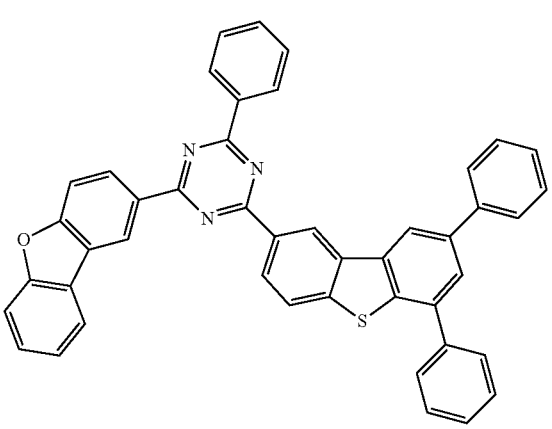
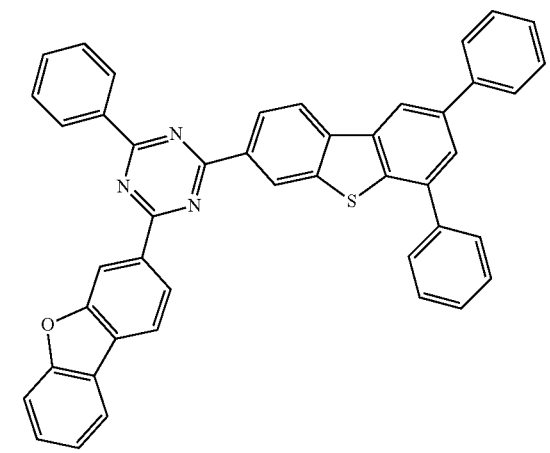
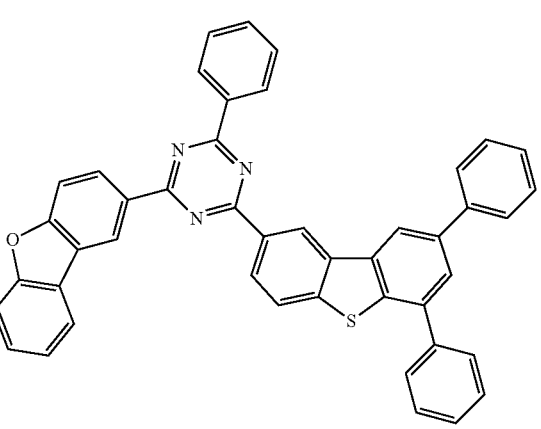
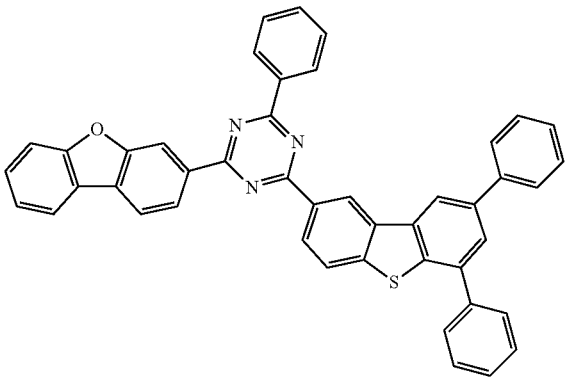
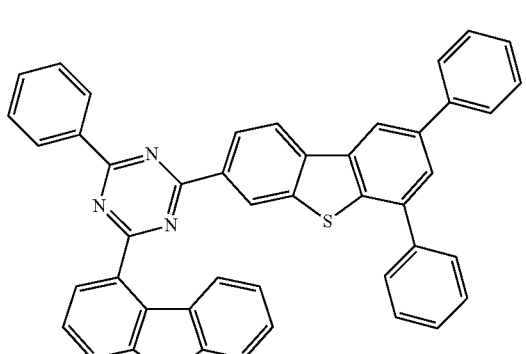
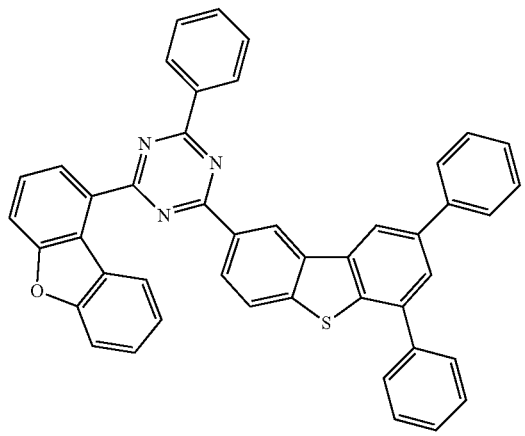

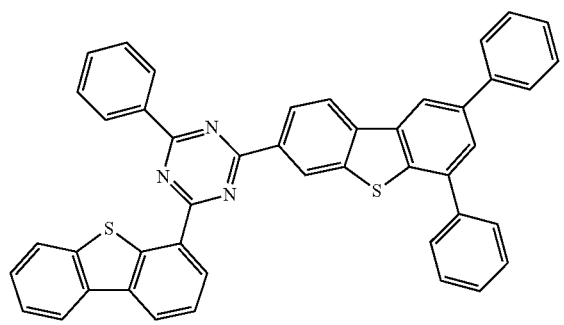
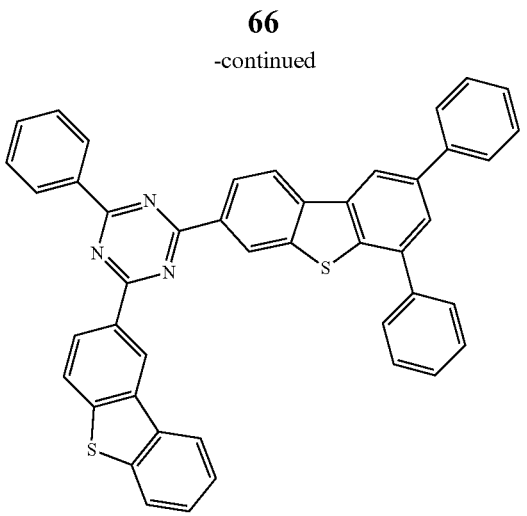
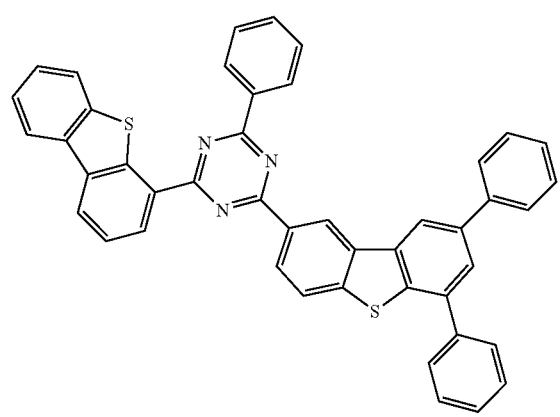
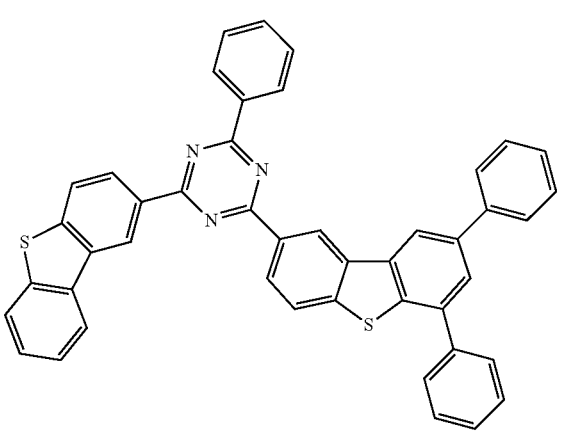
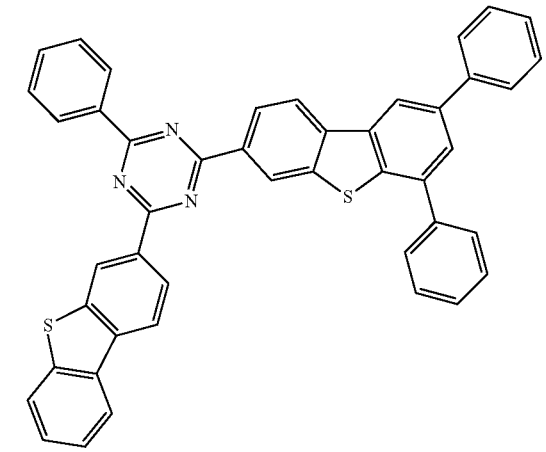
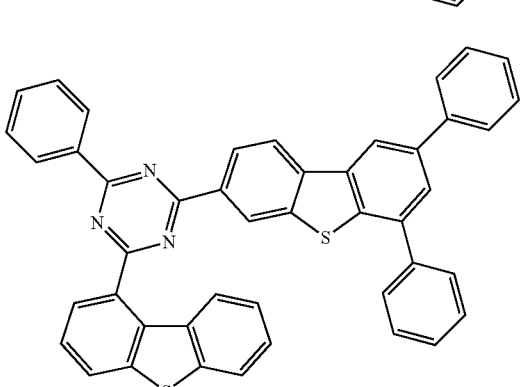
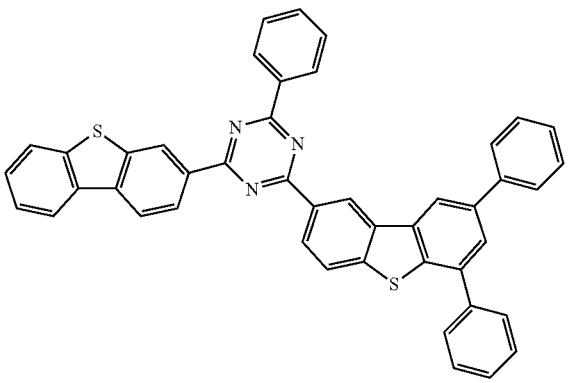
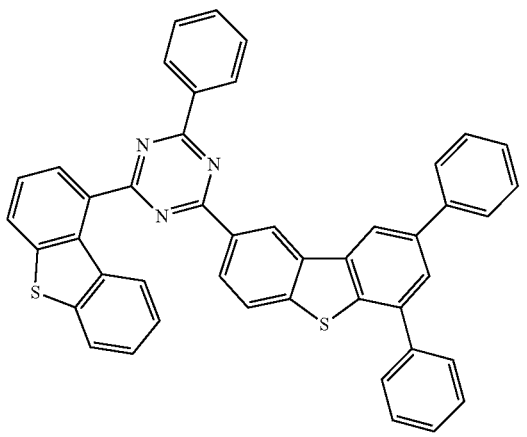

-continued

69
-continued
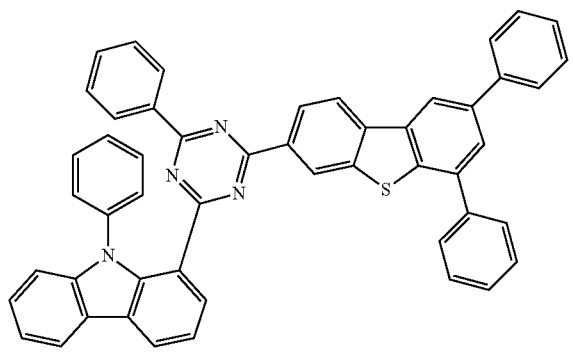
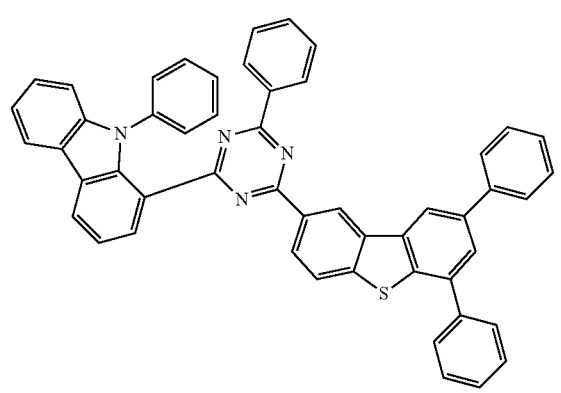
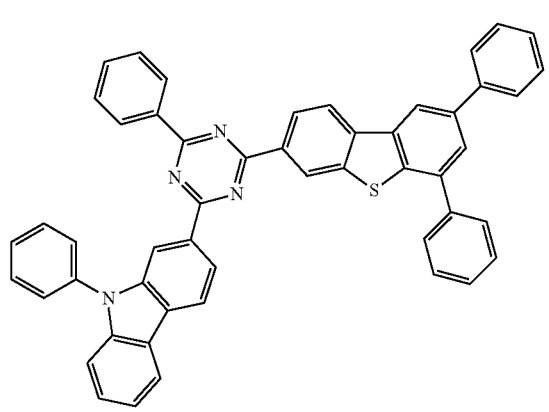
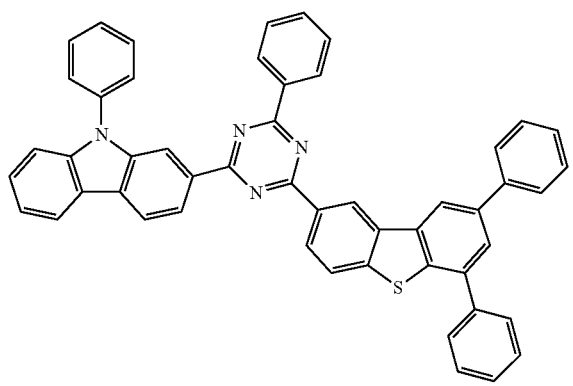
70
-continued
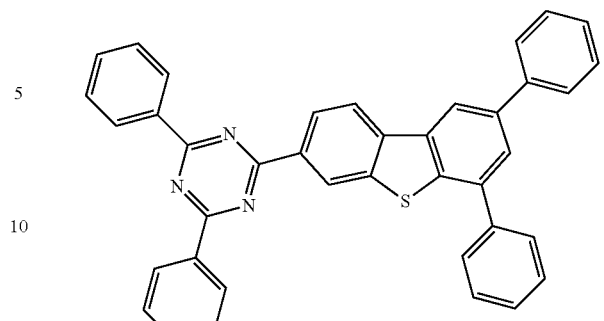
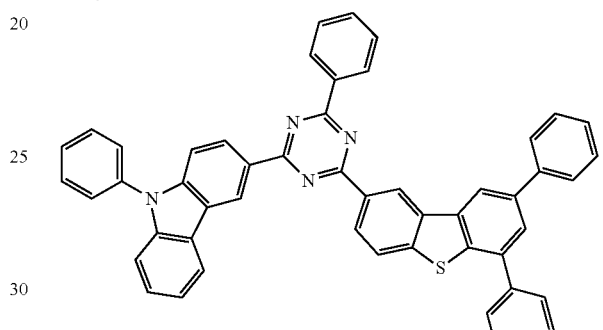
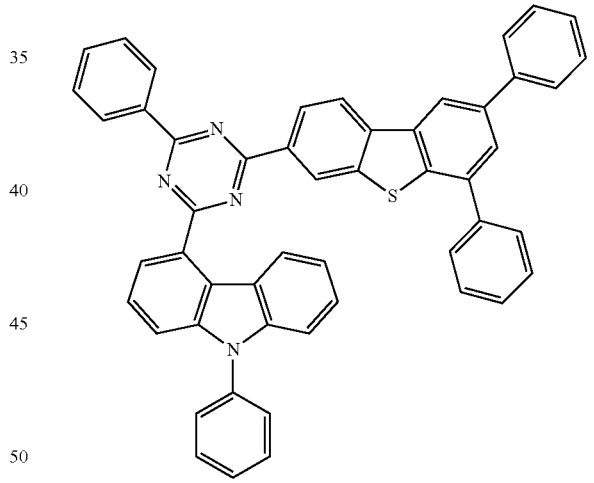
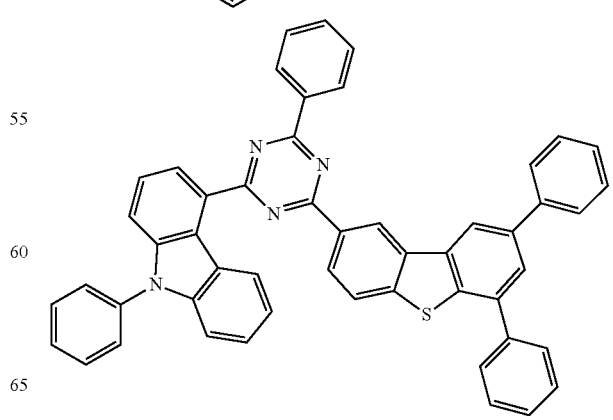

71
-continued
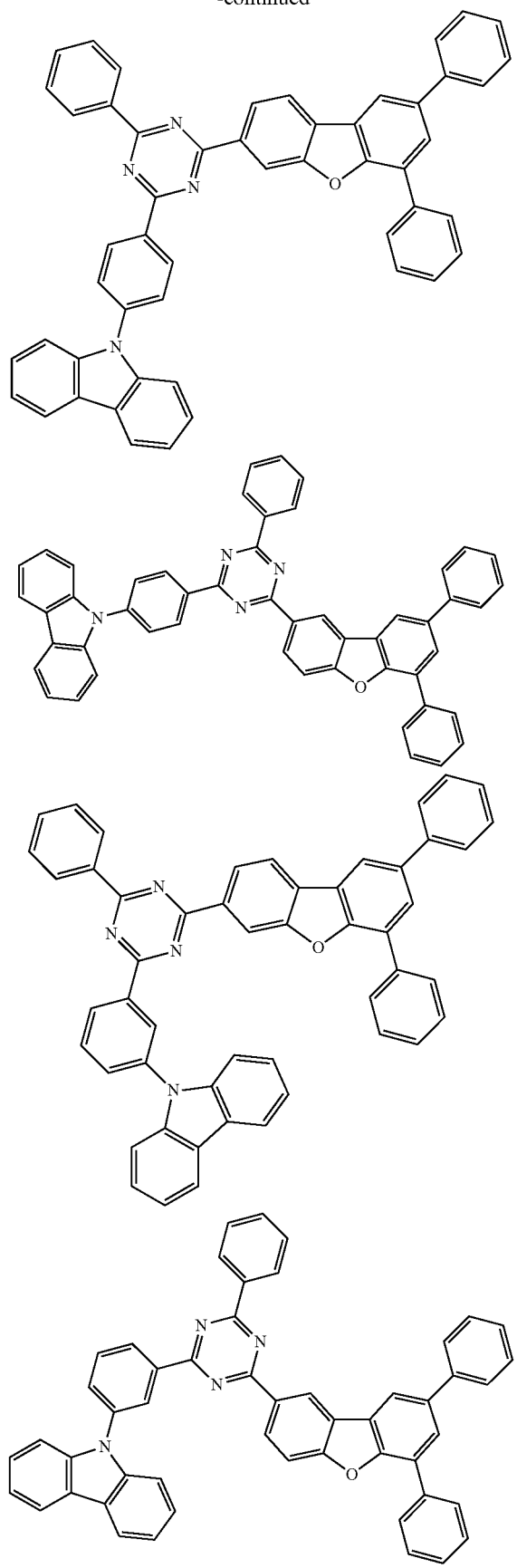
72
-continued
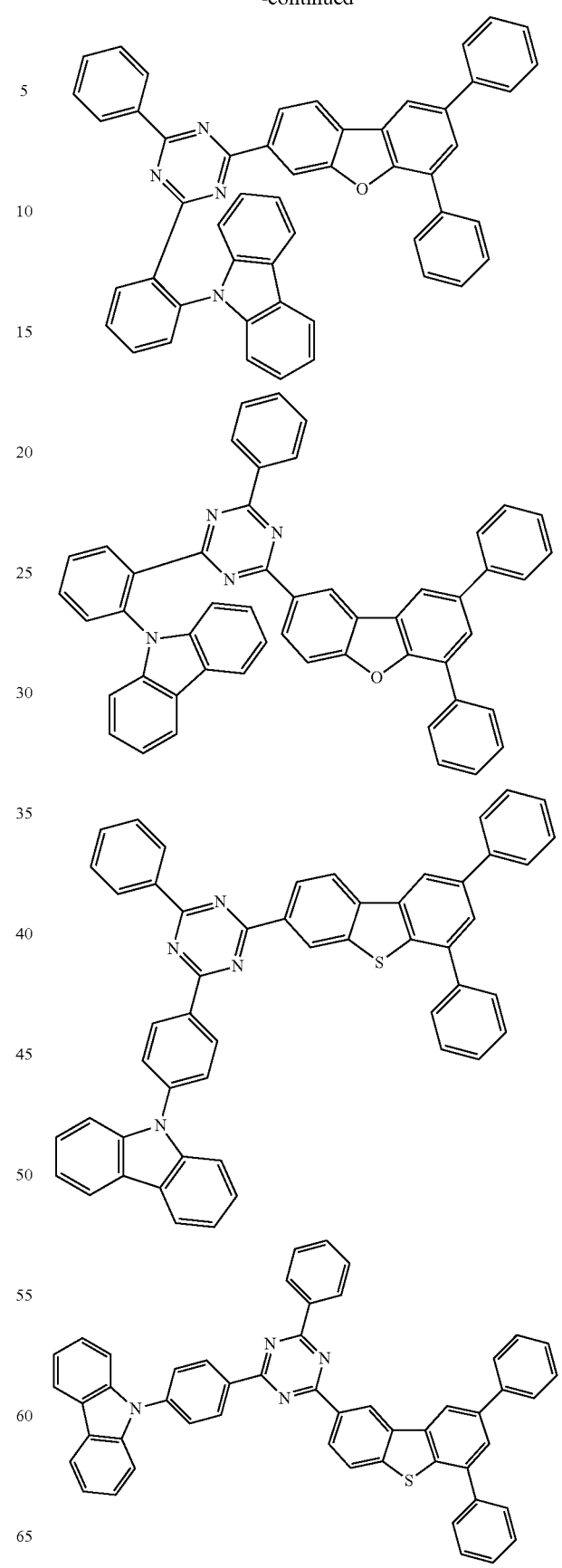

73
-continued
74
-continued
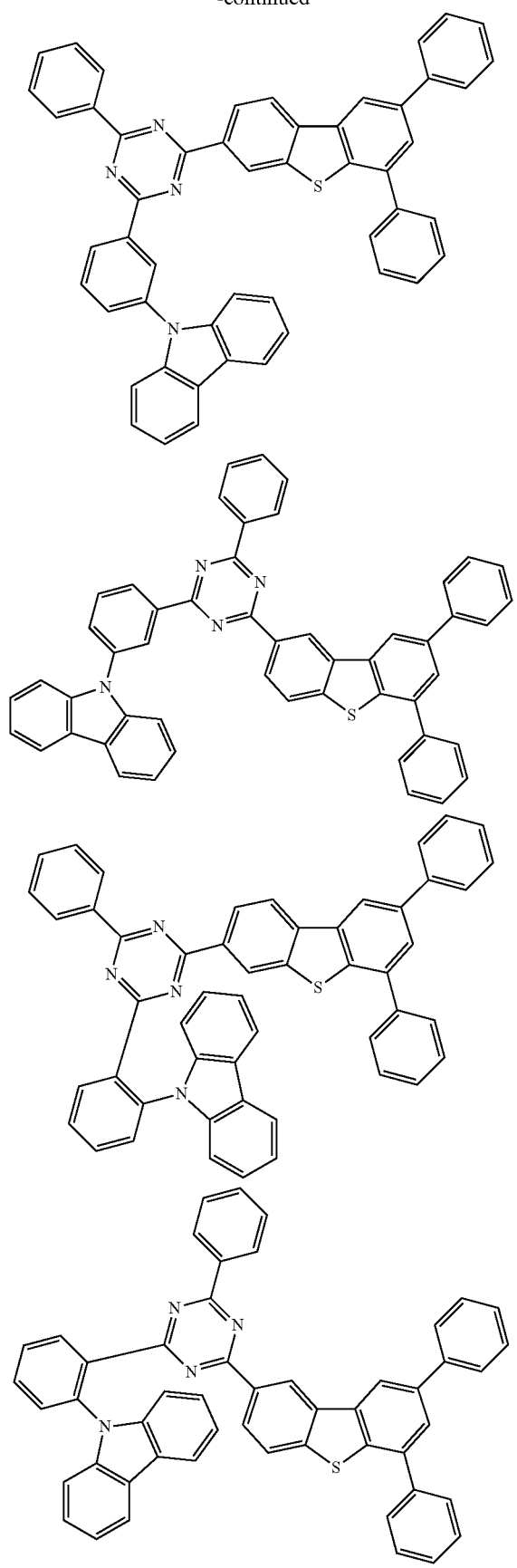
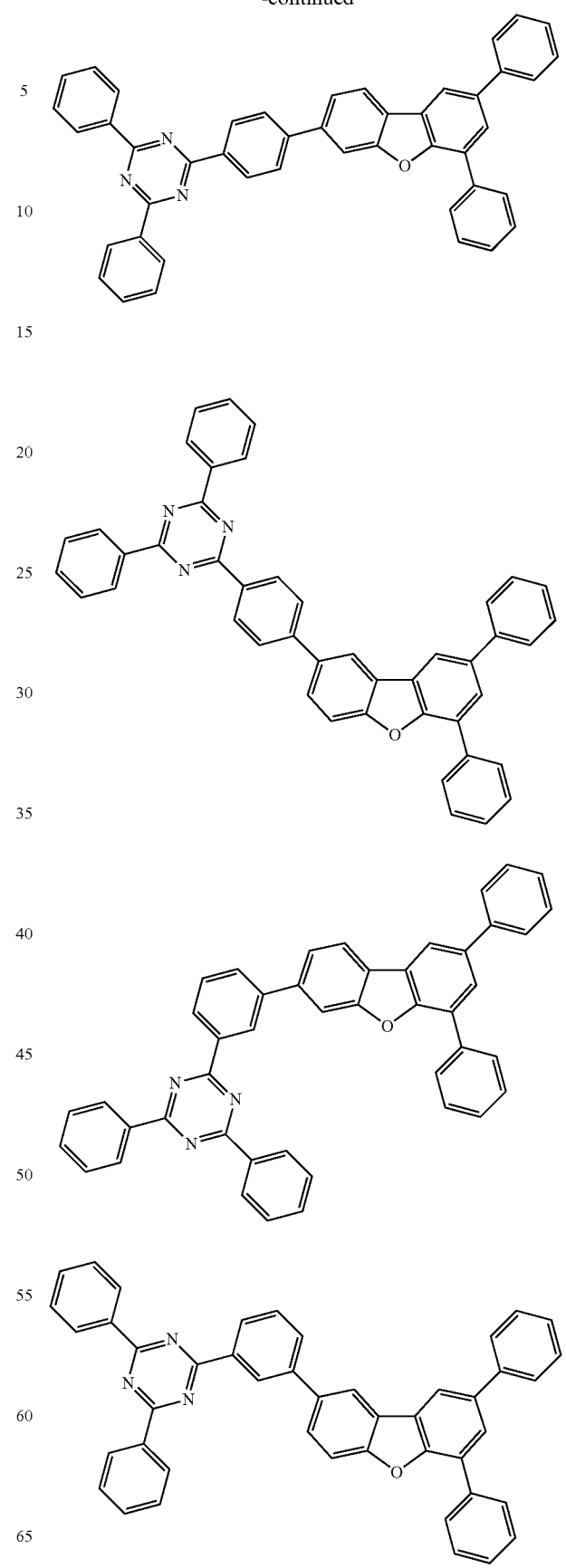

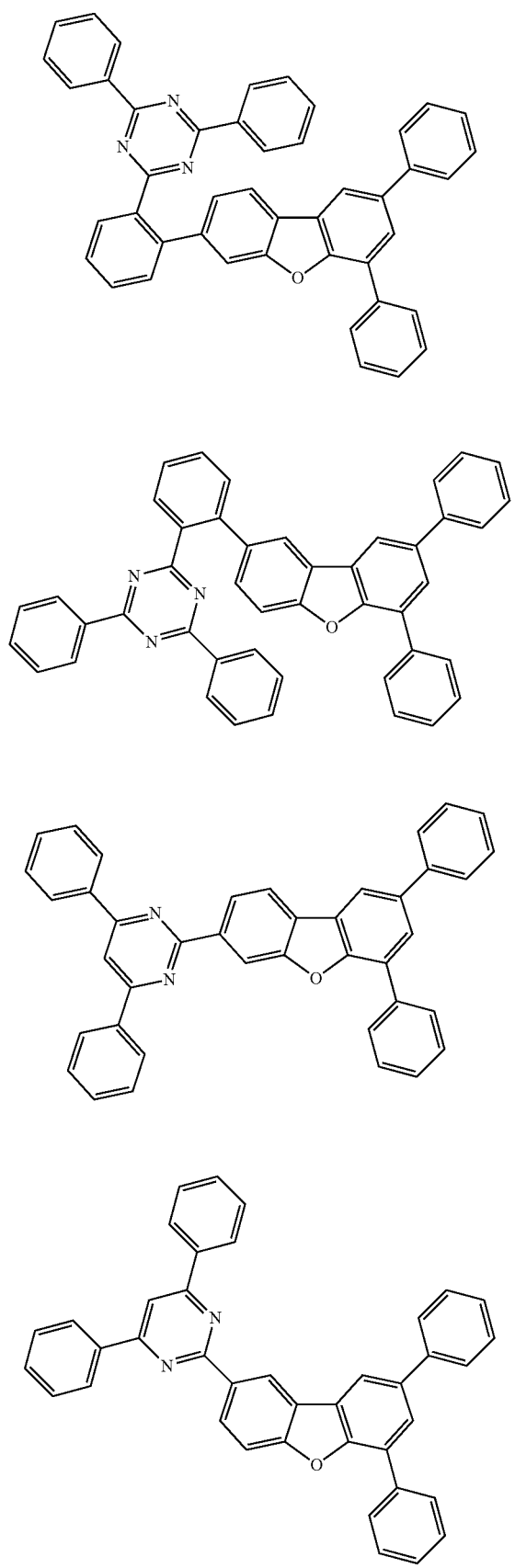
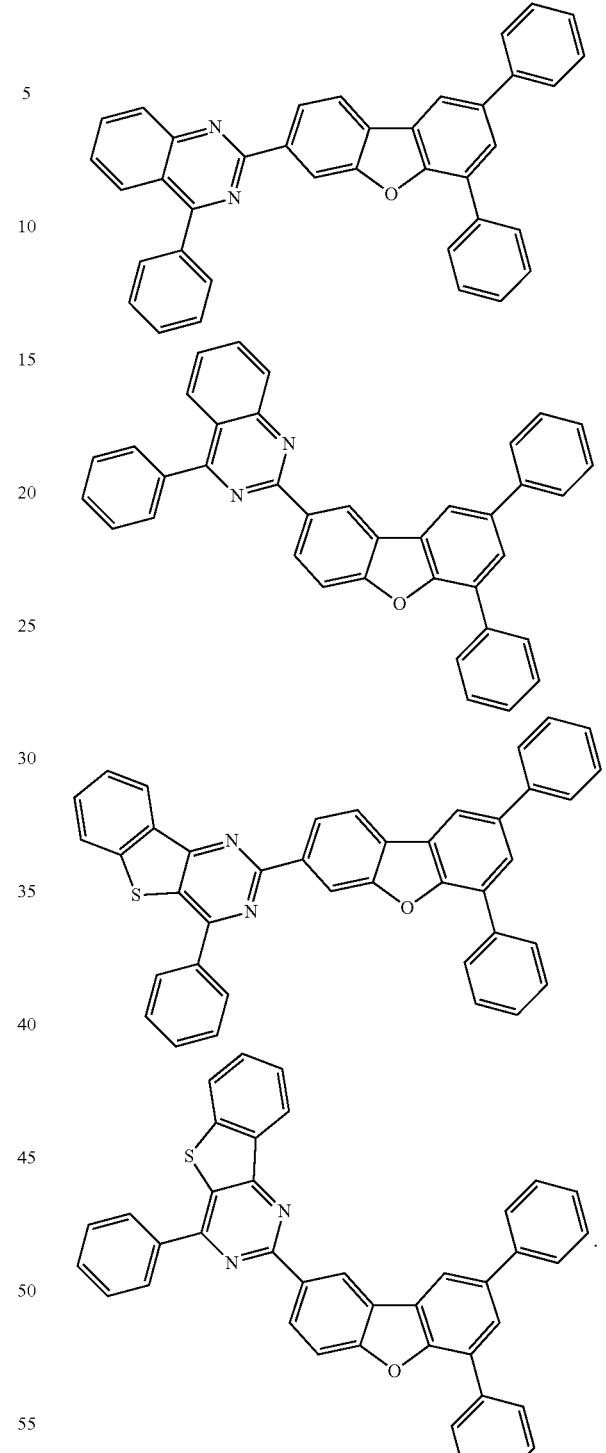
6. An organic light emitting device comprising a first electrode; a second electrode that is disposed opposite to the first electrode; and one or more organic material layers that are disposed between the first electrode and the second electrode, wherein one or more one layers of the organic material layers comprise the compound according to claim 1.
* * * * *